United States Patent [19]

Hart et al.

[11] Patent Number: 5,569,269
[45] Date of Patent: Oct. 29, 1996

[54] SURGICAL GRASPING AND SUTURING DEVICE AND METHOD

[75] Inventors: Rickey D. Hart, Plainville; John T. Rice, Lincoln, both of Mass.

[73] Assignee: Innovasive Devices, Inc., Marlborough, Mass.

[21] Appl. No.: 200,883

[22] Filed: Feb. 23, 1994

Related U.S. Application Data

[63] Continuation-in-part of Ser. No. 97,154, Jul. 26, 1993, abandoned.

[51] Int. Cl.[6] ............................................. A61B 17/04
[52] U.S. Cl. .................... 606/144; 606/148; 606/206; 606/207; 112/169
[58] Field of Search ................................. 606/205, 206, 606/207, 113, 148, 144, 145, 140, 141; 128/838, 840, 751; 223/104; 112/169

[56] References Cited

U.S. PATENT DOCUMENTS

| | | | |
|---|---|---|---|
| 2,114,695 | 4/1938 | Anderson | 606/206 |
| 3,828,791 | 8/1974 | Santos | 606/207 |
| 3,877,434 | 4/1975 | Ferguson et al. | 606/148 X |
| 3,967,625 | 7/1976 | Yoon | 606/206 X |
| 4,174,715 | 11/1979 | Hasson | 606/206 |
| 4,393,872 | 7/1983 | Reznik et al. | 128/752 X |
| 4,779,616 | 10/1988 | Johnson | 606/148 |
| 4,994,079 | 2/1991 | Genese et al. | 606/206 |
| 5,026,379 | 6/1991 | Yoon | 606/141 |
| 5,108,406 | 4/1992 | Lee | 606/206 X |
| 5,226,426 | 7/1993 | Yoon | 606/185 X |
| 5,257,637 | 11/1993 | El Gazayerli | 606/205 X |
| 5,281,220 | 1/1994 | Blake | 606/205 |
| 5,281,237 | 1/1994 | Gimpelson | 606/148 X |
| 5,312,422 | 5/1994 | Trott | 606/144 |
| 5,318,528 | 6/1994 | Heaven et al. | 606/205 X |
| 5,387,227 | 2/1995 | Grice | 606/148 X |

FOREIGN PATENT DOCUMENTS

| | | | |
|---|---|---|---|
| 537493 | 4/1993 | European Pat. Off. | 606/148 |
| 655682 | 4/1929 | France | 606/207 |
| 123563 | 6/1931 | Germany | 606/205 |
| 2758037 | 6/1979 | Germany | 128/840 |
| 4114204 | 11/1992 | Germany | 606/148 |
| 1657154 | 6/1991 | U.S.S.R. | 606/205 |
| 02493 | 3/1991 | WIPO | 606/206 |
| 21178 | 9/1994 | WIPO | 606/148 |

*Primary Examiner*—Michael H. Thaler
*Attorney, Agent, or Firm*—Pandiscio & Pandiscio

[57] ABSTRACT

A device for snaring cord-like objects and a methods for using same to pass portions of the cord-like objects through tissue are provided. The device includes a shaft containing a wire assembly having an object capturing device at its distal end. The wire assembly is reciprocally movable relative to the shaft between a first position wherein the capturing device is located within the distal portion of the shaft, and a second position wherein the capturing device extends distally outwardly from the distal end of the shaft. An activation device is attached to the proximal end of the shaft and the proximal end of the wire assembly so as to allow the controlled axial movement of the wire assembly relative to the shaft, and so as to allow the shaft and the wire assembly to be rotated as a unit about the longitudinal axis of the shaft. The methods include snaring and grasping a length of cord-like material and passing the cord-like material through one or more layers of tissue. More particularly, the shaft may be inserted through the tissue, grasp the cord-like material and pull the cord-like material back through the tissue as the shaft is disengaged therefrom. Alternatively, the cord-like material may be grasped by the device, inserted through the tissue along with the distal portion of the shaft, released from the distal end of the shaft, and left extending through the tissue when the shaft is withdrawn. Further, various combinations of these alternatives may be utilized in order to lace the cord-like material through the tissue in any particularly desired manner.

18 Claims, 45 Drawing Sheets

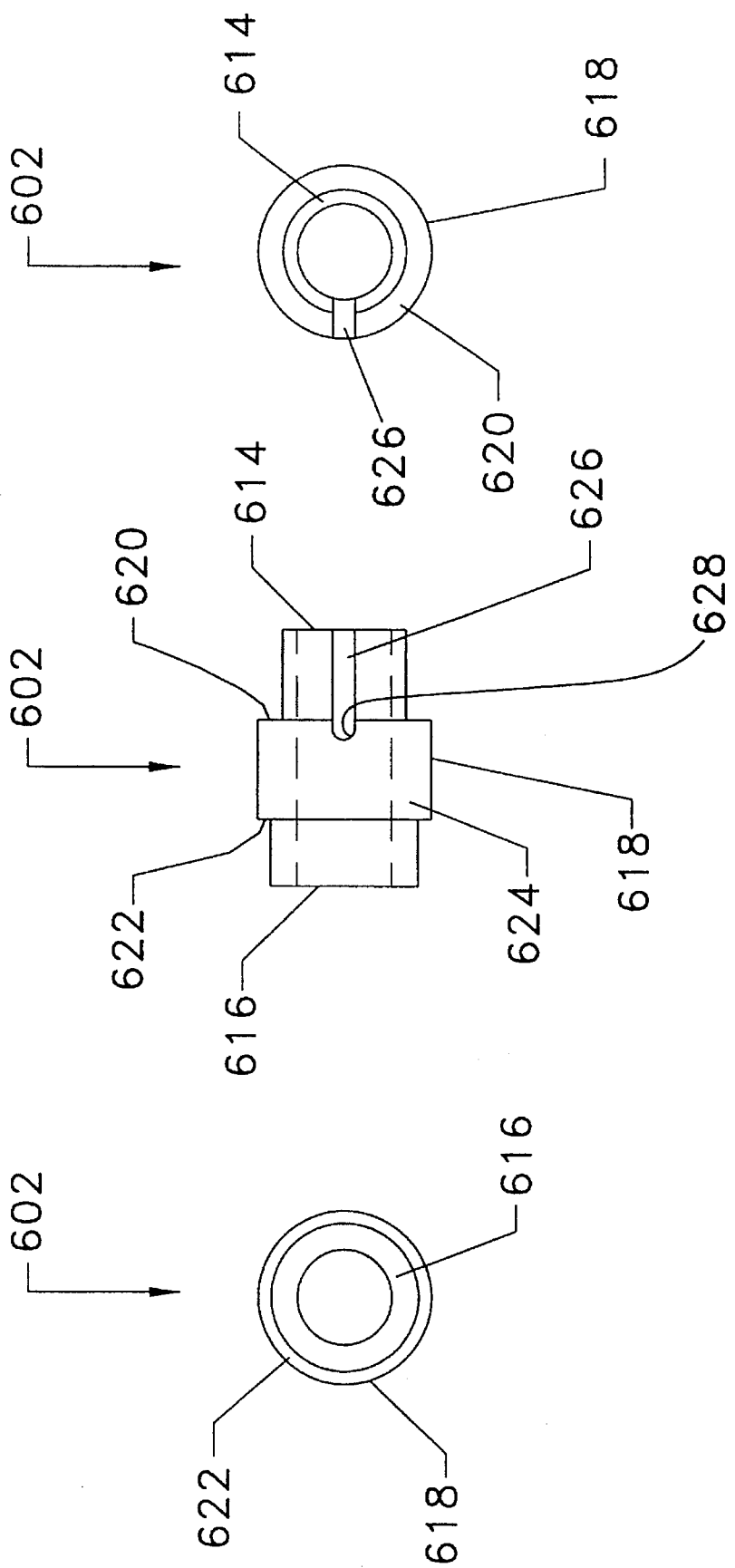

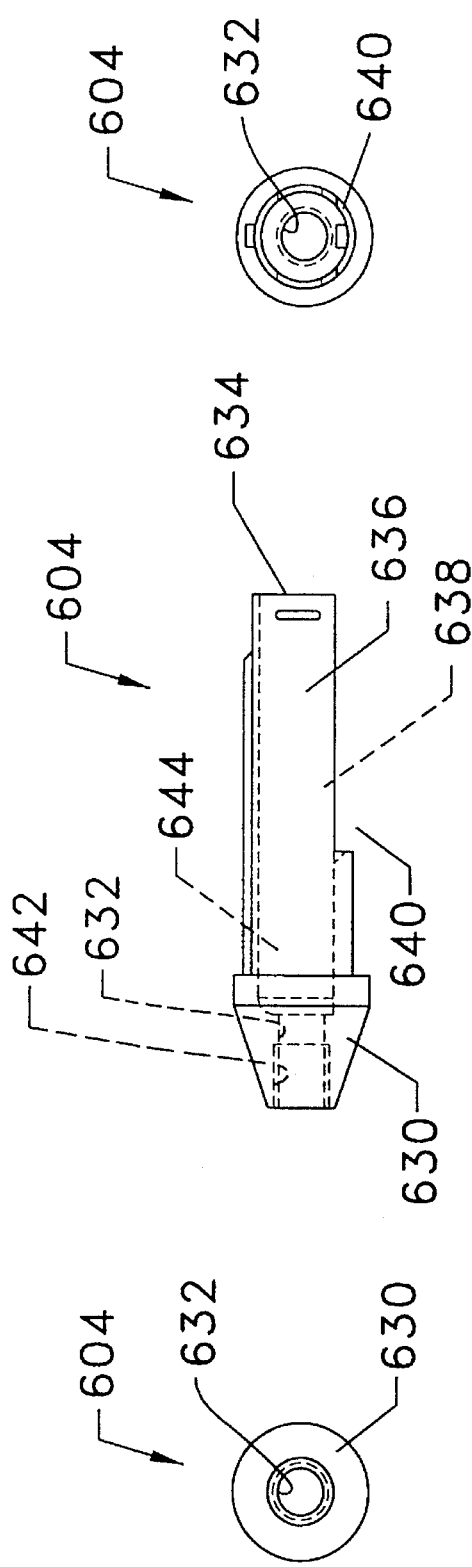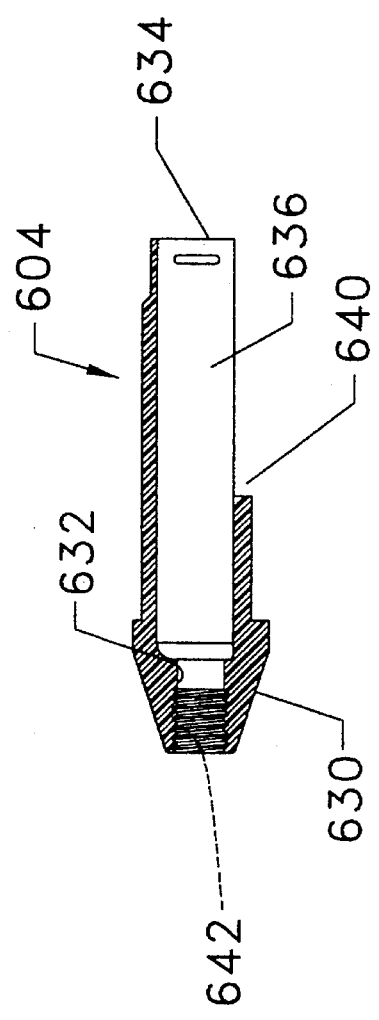

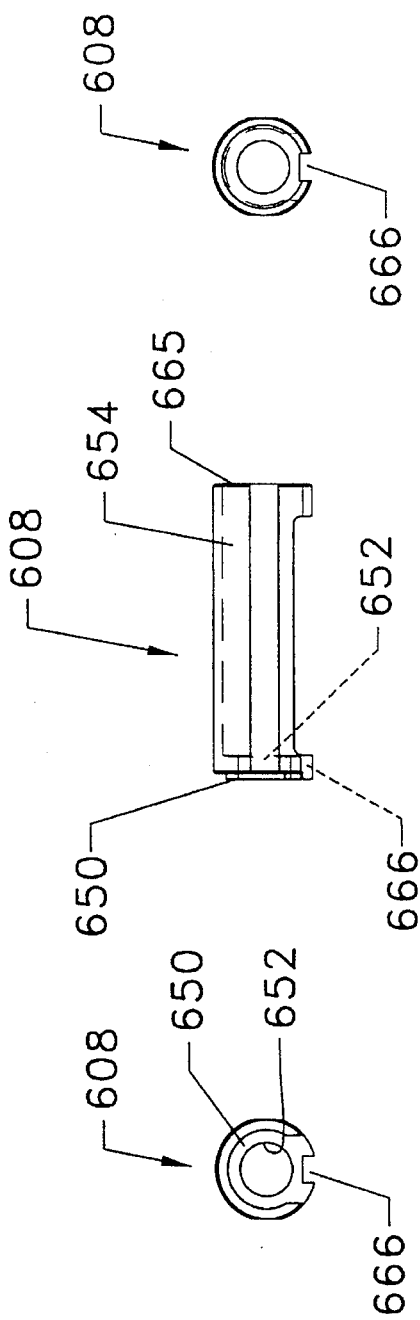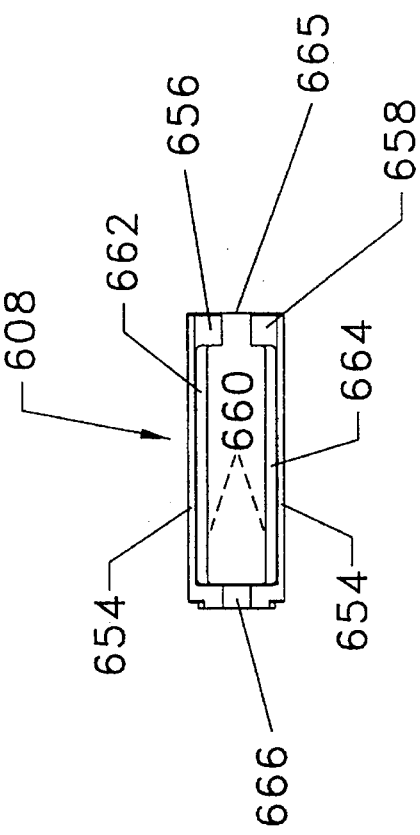

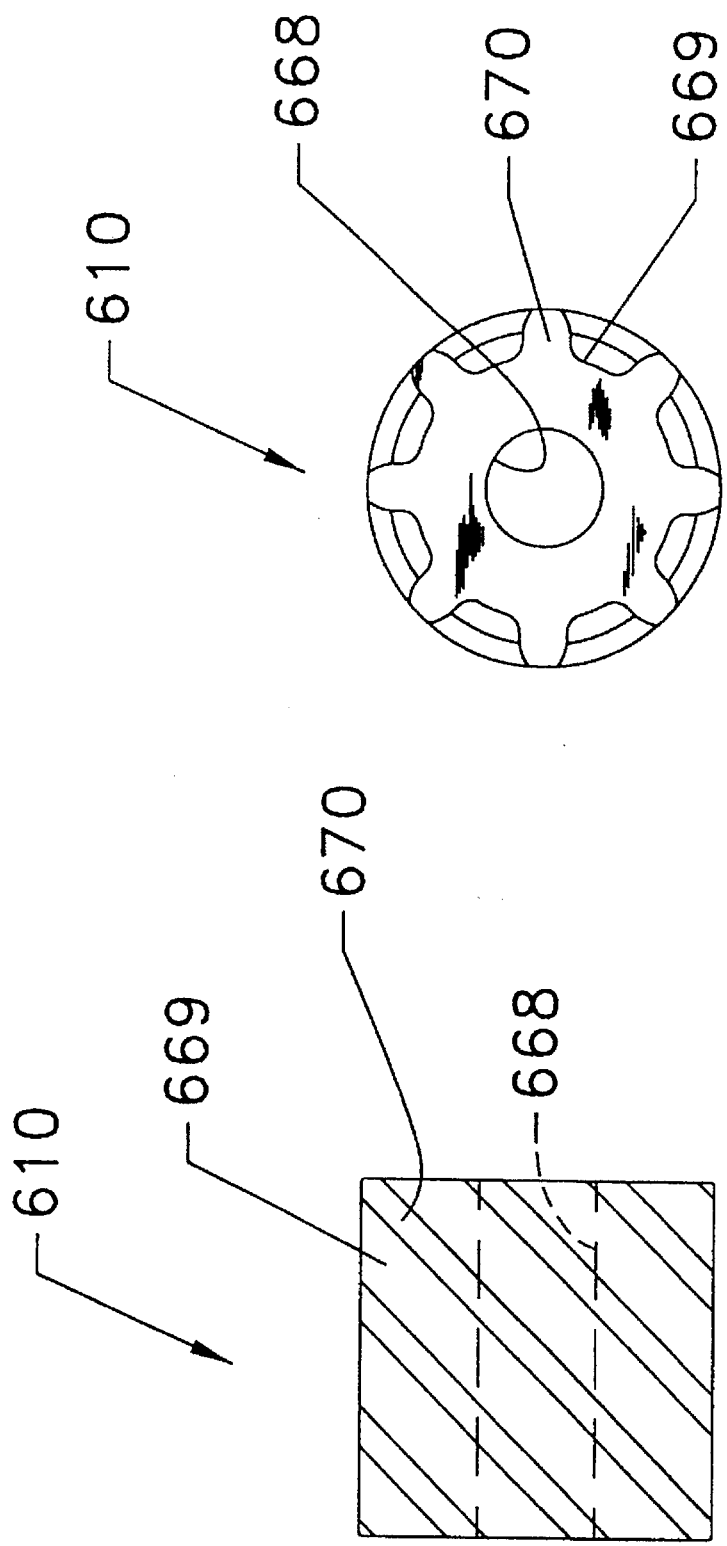

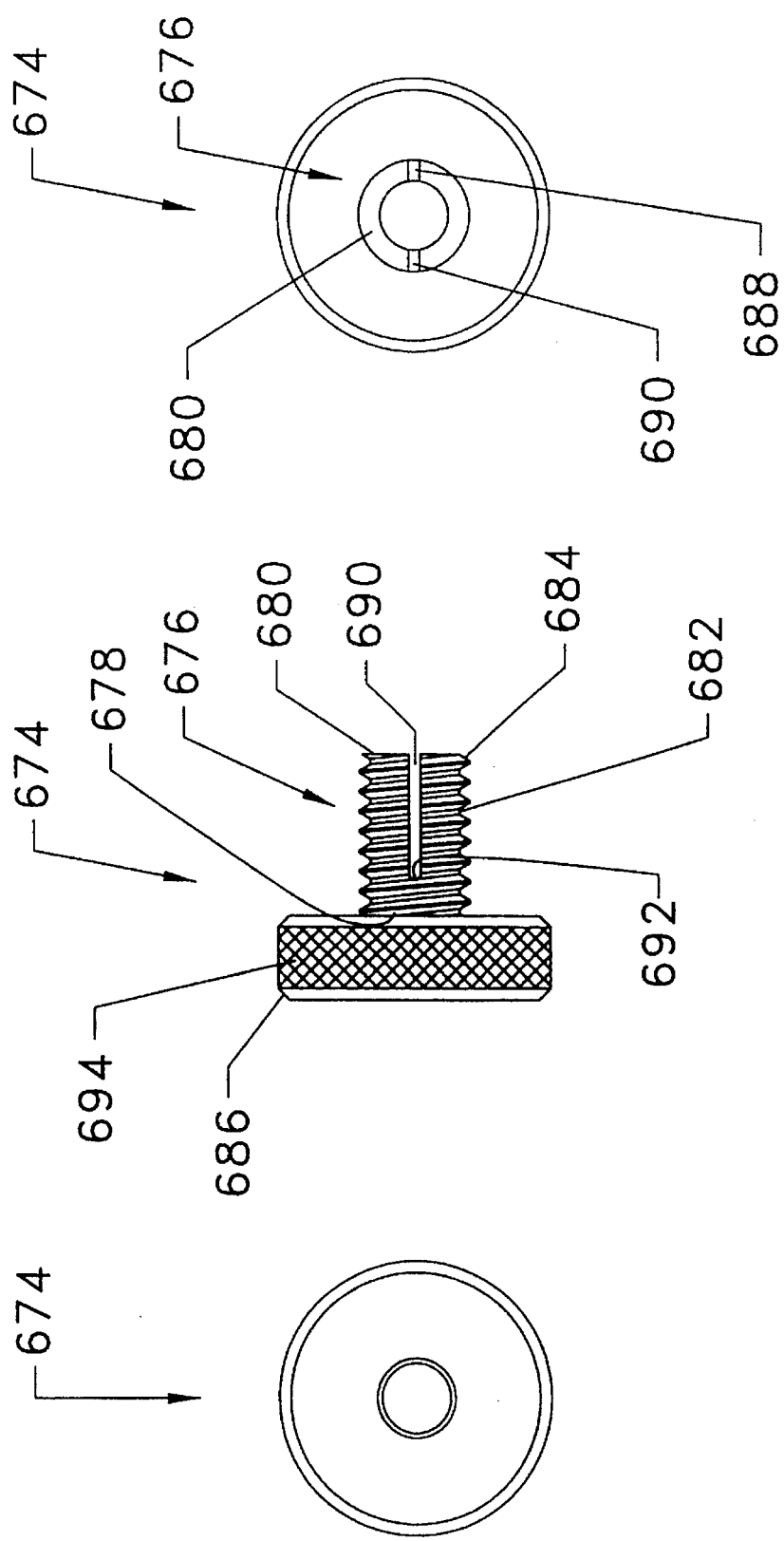

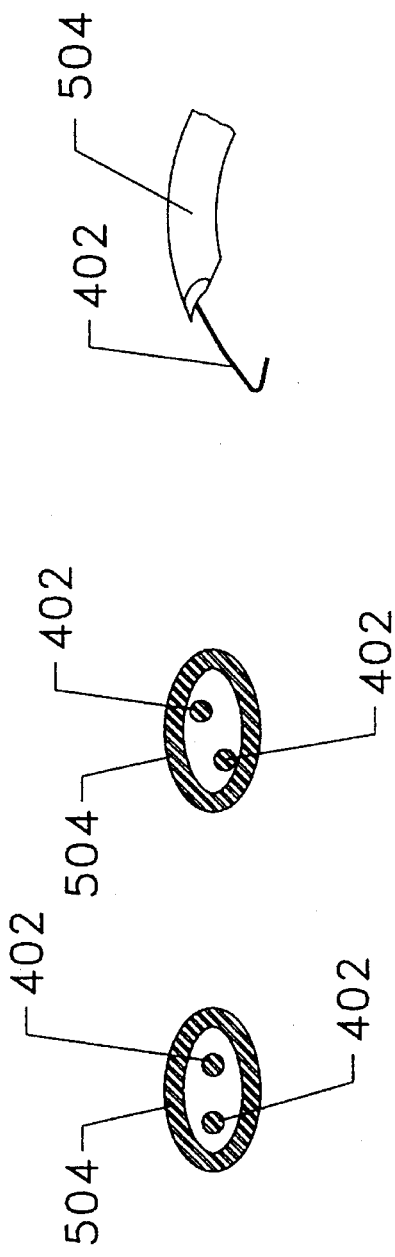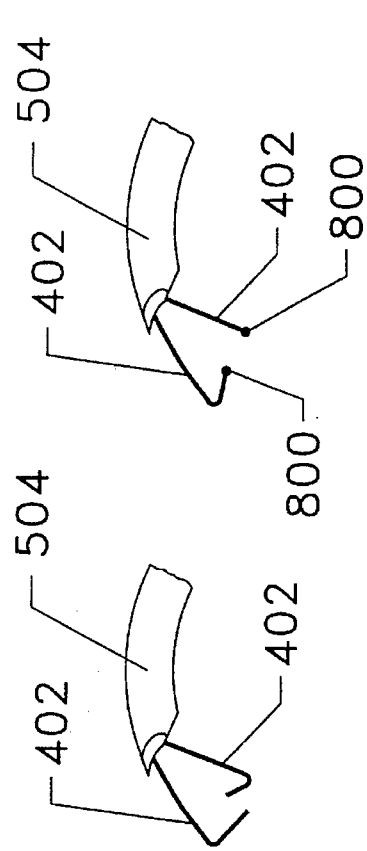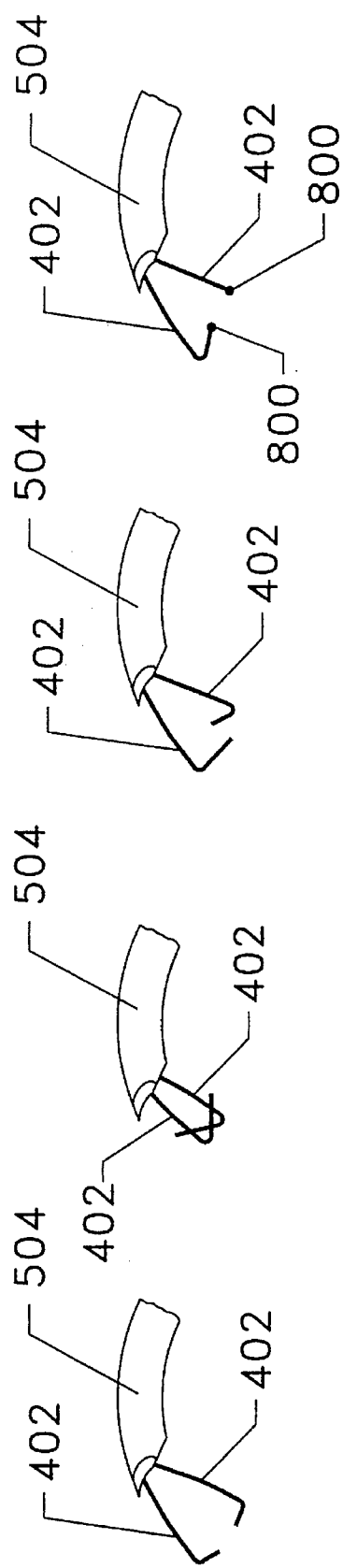

SURGICAL GRASPING AND SUTURING DEVICE AND METHOD

This is a continuation-in-part of prior, U.S. patent application Ser. No. 08/097,154, filed on Jul. 26, 1993, and entitled "Suture Grasping Device" now abandoned.

FIELD OF THE INVENTION

The present invention generally relates to devices for snaring suture or other cord-like or filament-like material, and for manipulating the snared suture during suturing procedures. More particularly, the present invention relates to suture grasping devices suitable for use in grasping a portion of a length of suture and drawing and/or pulling the suture through tissue in either open or closed surgical settings.

BACKGROUND OF THE INVENTION

Devices for grasping free suture ends during surgical procedures are well known in the art. In one such device, an elongated element is provided. This element has a flexible, closed loop at one of its ends. The elongate element is telescopically mounted inside a hollow shaft so that the loop can be alternately withdrawn into, or projected out of, the distal end of the shaft.

In use, this device is first set so that its loop is retracted into the shaft. Then the device is manipulated so that the distal end of the shaft is brought into the vicinity of a free end of the suture which is to be grasped. The loop then is projected out of the distal end of the shaft. The device is thereafter further manipulated so that the free end of the suture which is to be grasped extends through the loop. Finally, the loop surrounding the suture is retracted back into the shaft, thereby grasping the suture and holding it tightly against the distal end of the shaft.

While devices of the type described above work for their intended purpose, they also have several drawbacks. For example, it is often difficult (or impossible) to conveniently access a free end of a length of suture, even in those cases where some intermediate portion of the suture has been located. This is particularly true in closed surgeries where visibility is frequently quite limited and the available space at the surgical site is often restricted.

Furthermore, in many surgical procedures suture needs to be laced one or more times through one or more layers of tissue. Conventionally, such suturing is accomplished by attaching a needle to at least one free end of the suture. This needle is then manipulated using a needle holder so as to pass the suture through the tissue. Thereafter, a grasping device such as the one described above is used to snare a free suture end (or ends) for further manipulation or tying.

The need to use a needle and needle holder to pass the suture through the tissue, and the need to use a separate grasping device to complete the suturing operation, can be inconvenient and cumbersome. This is particularly true in closed surgical procedures where the surgeon must operate through a small passageway leading from the skin of the patient to an internal surgical site. In such situations, the surgeon's visual and physical access to the surgical site is generally quite limited.

OBJECTS OF THE INVENTION

Accordingly, one object of the present invention is to provide a suture grasping device adapted to easily and conveniently grasp a length of suture at any point along the suture's length.

Another object of the present invention is to provide a suture grasping device which may be used in both open and closed surgical procedures.

Still another object of the present invention is to provide a suture grasping device which is capable of securely snaring a length of suture.

And another object of the present invention is to provide a suture grasping device which is capable of snaring a length of suture and thereafter allowing limited movement of that suture relative to the device.

Yet another object of the present invention is to provide a suture grasping device which is adapted to pierce either soft tissue or relatively hard tissue (e.g. cartilage) substantially adjacent to the portion of the device which grasps the suture.

A further object of the present invention is to provide a suture grasping device which is adapted to either (i) pierce tissue prior to grasping a suture located on the far side of the tissue, or (ii) grasp a length of suture and thereafter pierce tissue, so that a length of suture may be passed through the tissue either as the device is withdrawn from the tissue or as it is urged therethrough.

And another object of the present invention is to provide a suture grasping device which comprises a suture snaring portion and a handle portion, wherein the orientation of the suture snaring portion relative to the handle portion may be adjusted during use.

And another object of the present invention is to provide a new method for passing suture through tissue.

Still another object of the present invention is to provide a new method for suturing tissue.

SUMMARY OF THE INVENTION

These and other objects of the present invention are addressed in one preferred embodiment by a suture grasping device which comprises a rigid, hollow shaft, a rod, a first elongate wire-like element, a second elongated wire-like element, and an actuation device.

More particularly, the rigid, hollow shaft includes a proximal end, a proximal portion adjacent to the proximal end, a pointed distal end, a distal portion adjacent to the distal end, and a lumen extending between the proximal end and the distal end. In this embodiment, the inner and outer diameters of the proximal portion of the shaft are larger than the inner and outer diameters of the distal portion of the shaft. Further, the distal portion of the shaft may be curved, if desired.

The rod is a solid element having a proximal end and a distal end. The rod is telescopically located in the proximal portion of the shaft. More specifically, the rod has a longitudinal length slightly greater than the longitudinal length of the proximal portion of the shaft. Accordingly, the rod may be moved between (i) a proximalmost position wherein the distal end of the rod is spaced proximally from the point where the proximal and distal portions of the shaft meet; and (ii) a distalmost position wherein the distal end of the rod is substantially aligned with the point where the proximal and distal portions of the shaft meet.

The first and second wire-like elements each have a proximal end and a distal end. The proximal ends of these two wire-like elements are attached to the distal end of the rod, whereby the two wire-like elements will move in conjunction with the rod. In addition, at least the distal portions of the two respective wire-like elements normally bend or flare away from each other. Furthermore, the first wire-like element is bent radially inwardly immediately adjacent to its distal end so as to form a substantially hook-shaped configuration.

The longitudinal lengths of the first and second wire-like elements are selected such that when the rod is in its proximalmost position, the distal ends of the first and second wire-like elements will be located within the distal portion of the shaft. In this position, the distal ends of the first and second wire-like elements will be disposed in closely spaced relation to one another. When the rod is in its distalmost position, however, the distal ends of the first and second wire-like elements will project out the distal end of the shaft. In this position, the distal ends of the first and second wire-like elements together form a substantially V-shaped configuration extending outwardly from the distal end of the shaft.

The actuation device is attached to the proximal end of the shaft and to the proximal end of the rod. In this first embodiment of the invention, the actuation device includes a housing attached to the proximal end of the shaft. The housing defines a cylindrical cavity which is aligned with, and opens axially into, the lumen of the shaft. A trigger is pivotally attached to the housing and extends into the cylindrical cavity. A piston-like element is attached to the proximal end of the rod, and located in reciprocally sliding relation within the housing's cylindrical cavity. A spring biases the piston-like element proximally so that the rod will normally assume its aforementioned proximalmost position. The piston-like element may be moved distally against the force of the spring by the trigger, so that the rod will assume its distalmost position.

It will, therefore, be understood that the rod normally resides in its proximalmost position and the distal ends of the two wire-like elements normally reside within the distal portion of the shaft. However, the distal ends of the two wire-like elements may be projected out the distal end of the shaft when desired using the trigger. It is also to be appreciated that when the distal ends of the two wire-like elements reside within the distal portion of the shaft, the pointed distal end of the shaft may be forced through tissue without interference from either the distal ends of the two wire-like elements or any suture which may be grasped thereby.

The foregoing suture grasping device may be used to grasp and manipulate a piece of suture at a surgical site. Among other things, it may also be used to grasp a piece of suture and to pass that suture through one or more layers of tissue. The passage of suture through tissue may be accomplished either by pulling the suture through, or by pushing the suture through, the tissue. Multiple passes of suture may be used to suture two pieces of tissue together.

More particularly, in those cases where it is desired to pull a suture through tissue, the pointed distal end of the shaft is first forced through the tissue. Then the shaft is manipulated so as to bring its distal end substantially adjacent to the portion of the suture which is to be carried back through the tissue. Next, the trigger is activated so as to move the rod toward its distalmost position. This causes the distal ends of the wires to project out the distal end of the shaft so that the two wire elements flare away from each other. The suture grasping device is then manipulated further as needed so as to position the suture in the gap between the first and the second wire-like elements.

The trigger is then released so as to allow the rod to return to its proximalmost position under the influence of the spring. As this occurs, the distal ends of the two wire-like elements retreat back into the distal portion of the shaft, with the two wire-like elements moving back toward one another as they re-enter the distal portion of the shaft. As the two wire-like elements retract, the hook at the distal end of the first wire-like element grapples the suture which is located between the two wire-like elements and carries it toward the distal end of the shaft. As the hook enters the distal end of the shaft, a portion of the suture is also drawn into the distal end of the shaft. The suture is captured in this position by the spring-biased hook acting in co-operation with the distal end of the shaft. If desired, the hook, the shaft and the suture may be sized so that the suture is tightly bound to the shaft at this point. Alternatively, the hook, the shaft and the suture may be sized so that the suture will be free to slide transversely relative to the hook when it is inside the distal portion of the shaft.

The distal end of the shaft is then withdrawn from the pierced tissue, carrying the grappled suture with it. Thereafter, the length of suture is released from the suture grasping device by squeezing the trigger again. This causes the wire-like elements to project out the distal end of the shaft in flaring relation to one another. The suture then is released from the suture grasping device by manipulating the tool and/or the suture so that the suture no longer sits in the gap between the distal ends of the two wire-like elements.

In those cases where it is desired to push a suture through tissue, a corresponding procedure is used. Specifically, the distal end of the shaft is first positioned substantially adjacent to the suture which is to be passed through the tissue. The trigger then is squeezed so as to project the two wire-like elements out the distal end of the shaft, in flaring relation to one another. Thereafter, the device is manipulated so as to position the suture in the gap between the two wire-like elements. The trigger is then released so as to allow the distal ends of the two wire-like elements to retract back into the distal portion of the shaft under the influence of the spring, with the two wire-like elements moving back toward one another as they re-enter the distal end of the shaft. As this occurs, the hook grapples the suture and holds it against the distal portion of the shaft. The engagement of the suture with the distal end of the shaft is such that the point at the distal end of the shaft is located distally of the grasped suture and the two wire-like elements.

In this configuration, the distal end of the shaft is then forced through the tissue, carrying the grappled suture with it. Once the distal end of the shaft is on the far side of the tissue, the trigger is squeezed again so as to project the two wire-like elements out the distal end of the shaft, in flaring relation to one another. The suture is then released from the suture grasping device by manipulating the tool and/or the suture so that the suture no longer sits in the gap between the distal ends of the two wire-like elements. Then the trigger is released so as to retract the distal ends of the two wire-like elements into the distal end of the shaft. Finally, the shaft is withdrawn from the tissue, leaving the suture extending through the tissue.

A suturing procedure requiring multiple passes of the suture through one or more layers of tissue can also be conveniently accomplished with the present invention. For example, the suture grasping device might be used to first pull a length of suture through the tissue, and thereafter to push that same suture through the tissue at a location adjacent to the first pass of the suture through the tissue. Alternatively, the suture grasping device may be used to first push a length of suture through the tissue, and thereafter to pull that same suture through the tissue at a location adjacent to the first pass of the suture through the tissue.

In some circumstances it may be desirable to adjust the orientation of the distal portion of the shaft without changing the orientation of the tool's handle. To this end, the present invention further contemplates that the actuation means may include means for rotating the shaft about its longitudinal axis as well as means for moving the two wire-like elements relative to the distal end of the shaft. In this alternative embodiment, the shaft extends through the housing and is in rotatable, but not axially movable, relation to the piston-like element. A gear is mounted on a portion of the shaft extending through the piston. Further, a second trigger, carrying a plurality of teeth, is pivotally attached to the housing so that its teeth extend into the cylindrical cavity, in engagement with the flights of the gear. Squeezing the second trigger causes movement of the teeth, which in turn drives the gear so as to rotate the shaft.

The two wire-like elements are contained within a tube. This tube has a portion adjacent to its proximal end which is bent at a 90° angle to the major longitudinal axis of the tube. The proximal ends of the two wire-like elements are affixed to the proximal end of the tube, and the flared distal portions of the two wire-like elements extend outwardly from the distal end of the tube. The major leg of the tube is reciprocally located in the shaft. The bent, minor leg of the tube extends radially outwardly through a slot formed in the shaft and is attached to a bearing. This bearing is attached to the distal wall of the piston-like element so that the bearing can rotate relative to the piston-like element. Further, the various elements are sized relative to one another such that (i) the distal end wall of the piston-like element is located substantially adjacent to the proximal end of the slot when the piston-like element is in its proximalmost position, and (ii) the distal end wall of the piston-like element is located substantially adjacent to the distal end of the slot when the piston-like element is in its distalmost position. In addition, the length of the two wire-like elements are selected such that their respective distal ends reside within the distal end of the shaft when the piston-like element is in its proximalmost position, and extend outwardly in flared relation to one another when the piston-like element is in its distalmost position.

With this alternative embodiment of the invention, the grasping and suturing functions of the device operate in substantially the same manner as set forth above. However, with this second embodiment of the invention, the shaft and the two wire-like elements contained in the shaft may be rotated about the tool's longitudinal axis without adversely affecting the remaining operations of the device.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 40 is a side view of a shaft bearing suitable for use in the grasper assembly shown in FIG. 35;

FIG. 41 is a left end view of the shaft bearing shown in FIG. 40;

FIG. 42 is a right end view of the shaft bearing shown in FIG. 40;

FIG. 43 is a side view of an outer housing suitable for use in the grasper assembly shown in FIG. 35;

FIG. 44 is a left end view of the outer housing shown in FIG. 43;

FIG. 45 is a right end view of the outer housing shown in FIG. 43;

FIG. 46 is a side view in section of the outer housing shown in FIG. 43;

FIG. 47 is a side view of an inner housing suitable for use in the grasper assembly shown in FIG. 35;

FIG. 48 is a left end view of the inner housing shown in FIG. 47;

FIG. 49 is a right end view of the inner housing shown in FIG. 47;

FIG. 50 is a bottom view of the inner housing shown in FIG. 47;

FIG. 51 is a side view of a gear suitable for use in the grasper assembly shown in FIG. 35;

FIG. 52 is an end view of the gear shown in FIG. 51;

FIG. 55 is a side view of a lock nut suitable for use in the grasper assembly shown in FIG. 35;

FIG. 56 is a left end view of the lock nut shown in FIG. 55;

FIG. 57 is a right end view of the lock nut shown in FIG. 55;

FIG. 58 is a sectional view of the distal end of the shaft;

FIG. 59 is a sectional view of the distal end of an alternative form of the shaft;

FIG. 60 is a side view of the distal end of another form of suture grasping device, wherein the device comprises just one hooked wire-like element;

FIG. 61 is a side view of the distal end of yet another form of suture grasping device, wherein the device comprises a pair of hooked wire-like elements;

FIG. 62 is a side view of the distal end of still another form of suture grasping device, wherein the device comprises a pair of hooked wire-like elements and further wherein the hooks are formed so that they overlap one another;

FIG. 63 is a side view of the distal end of yet another form of suture grasping device, wherein the device comprises a pair of hooked wire-like elements, and further wherein the hooks are formed so that the hook of one wire-like element will reside within a projection of the hook of the other wire-like element; and;

FIG. 64 is a side view of the distal end of still another form of suture grasping device, wherein the ends of the two wire-like elements include ball-like enlargements.

DETAILED DESCRIPTION OF THE PREFERRED EMBODIMENTS

Figure 1:
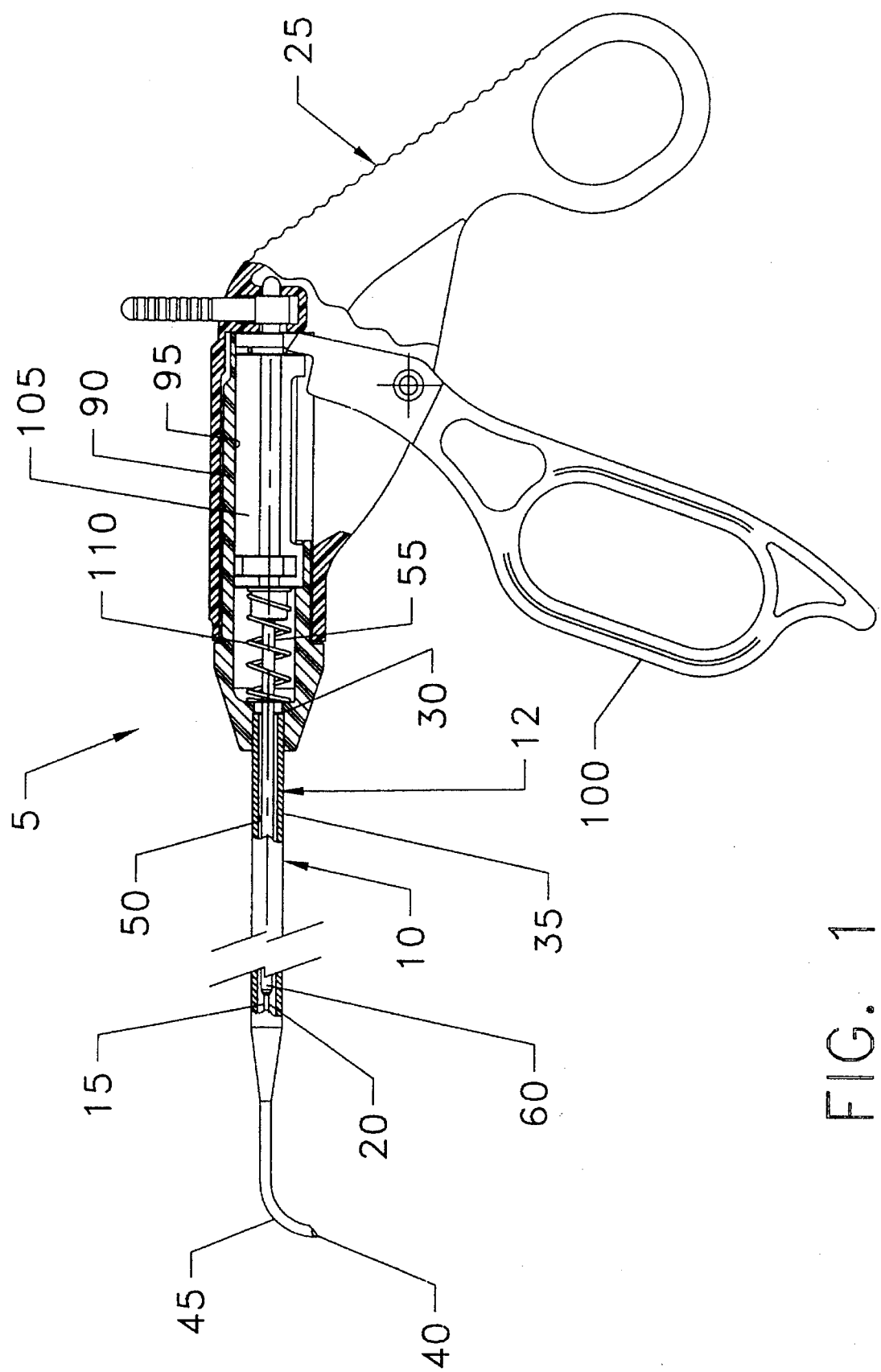
FIG. 1 is a side view, partially cut away and partially in section, of a suture grasping device formed in accordance with the present invention, wherein the rod is shown in its aforementioned proximalmost position.
Figure 2:
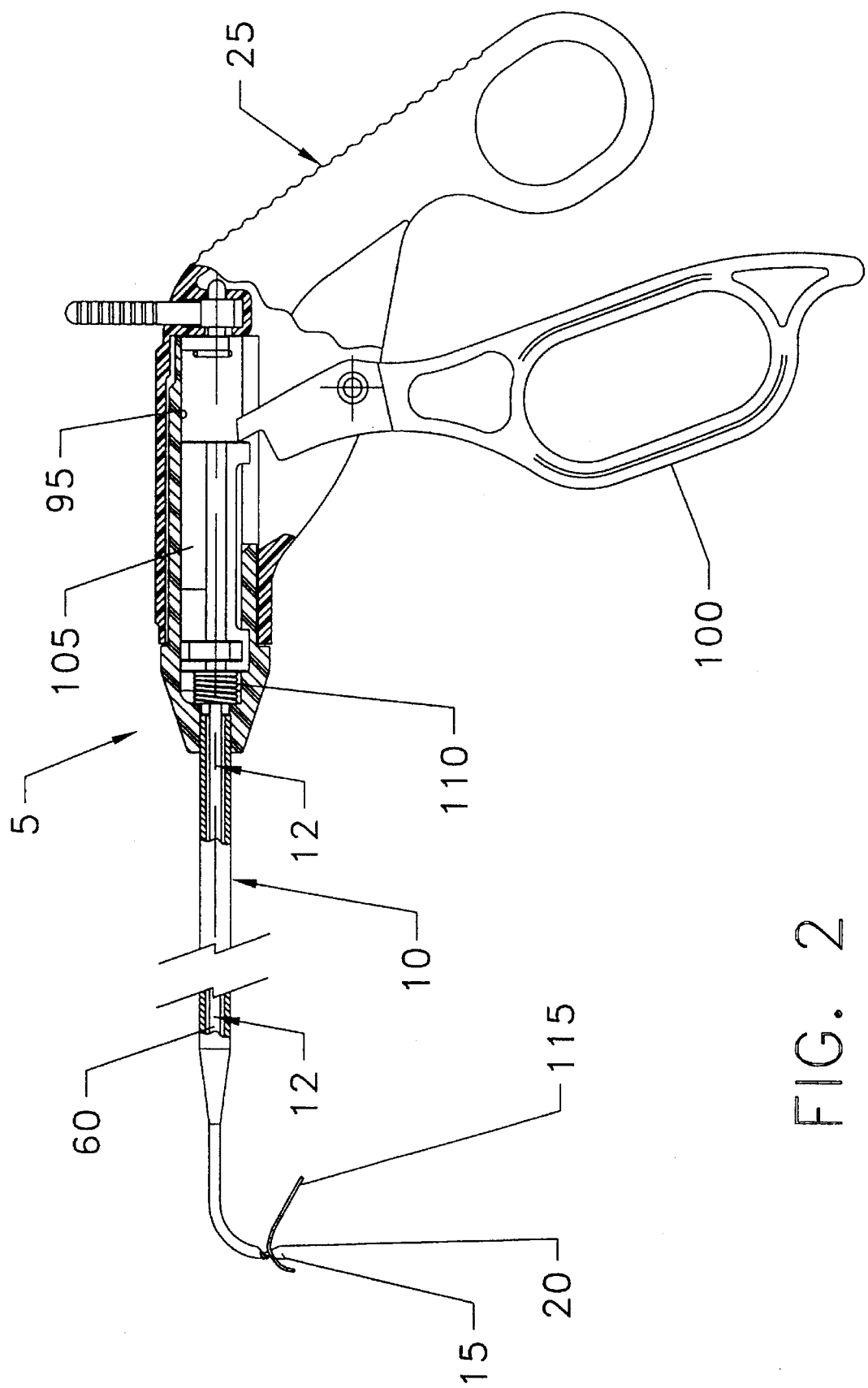
FIG. 2 is a side view, partially cut away and partially in section, of the device shown in FIG. 1, wherein the rod is shown in its aforementioned distalmost position.

Referring now to the drawings, and particularly to FIGS. 1 and 2, a suture grasping tool 5 is shown which comprises a rigid, hollow shaft 10, a rod 12, a first elongated wire-like element 15, a second elongate wire-like element 20, and an actuation device 25.

More particularly, the rigid, hollow shaft 10 includes a proximal end 30, a proximal portion 35 adjacent to proximal end 30, a pointed distal end 40, a distal portion 45 adjacent to distal end 40, and a central lumen 50 extending between proximal end 30 and distal end 40. In a preferred embodiment of the invention, the inner and outer diameters of proximal portion 35 of shaft 10 are larger than the respective inner and outer diameters of distal portion 45 of shaft 10. In accordance with one preferred embodiment of the invention, distal portion 45 of shaft 10 is curved. Of course, it should also be appreciated that distal portion 45 of shaft 10 could be formed straight if preferred.

Rod 12 is a solid element having a proximal end 55 and a distal end 60. Rod 12 is telescopically located in the proximal portion 35 of shaft 10. More specifically, rod 12 has a longitudinal length slightly greater than the longitudinal length of proximal portion 35 of shaft 10. Accordingly, rod 12 may be moved between (i) a proximalmost position wherein distal end 60 of rod 12 is spaced proximally from the point where the proximal and distal portions of shaft 10 meet (see FIG. 1); and (ii) a distalmost position wherein the distal end 60 of rod 12 is substantially aligned with the point where the proximal and distal portions of shaft 10 meet (see FIG. 2).

Figure 4:
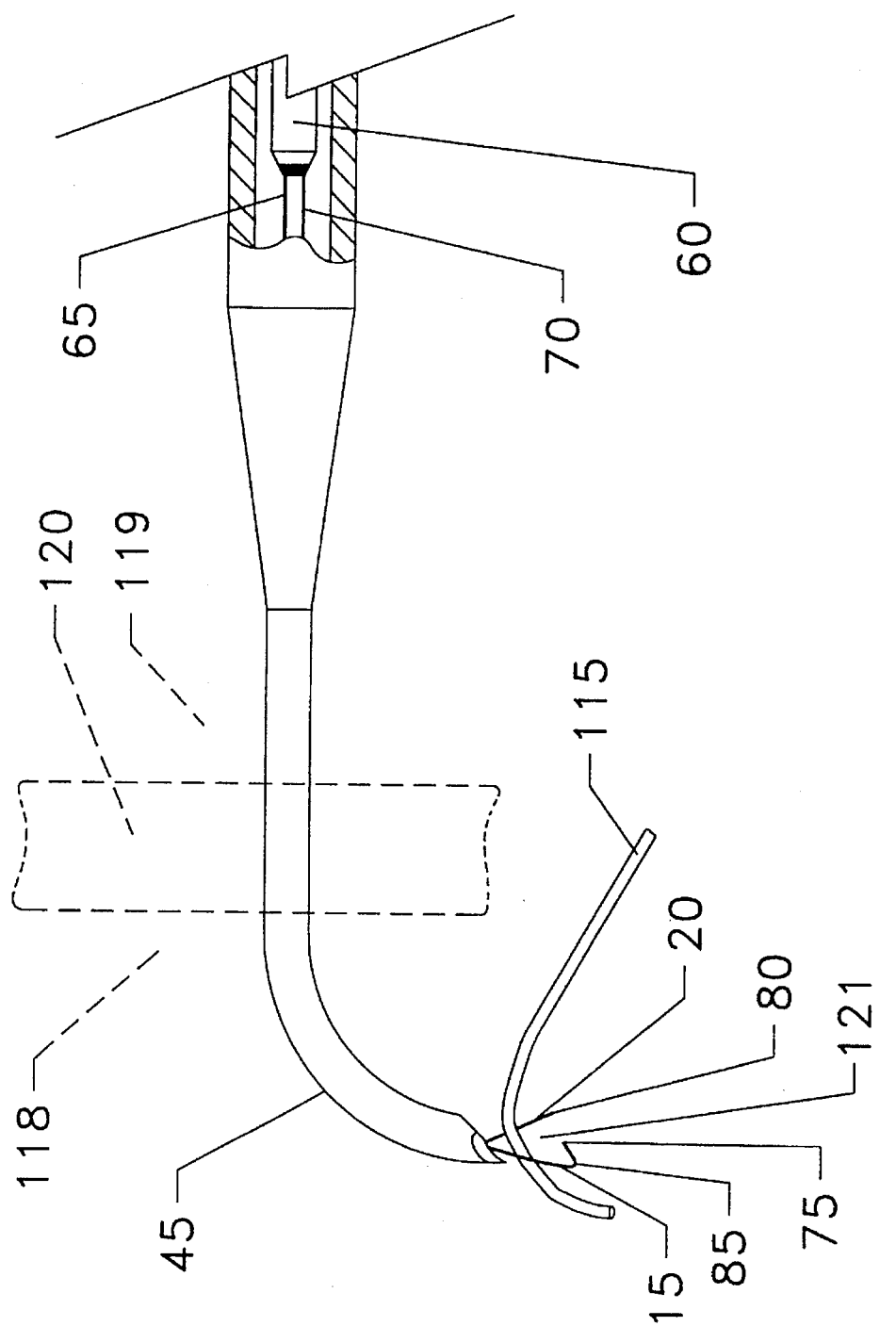
FIG. 4 is an illustrative side view similar to that of FIG. 3, except that the shaft is shown extending through the tissue, and the two wire-like elements are located in their fully extended, flared configuration flanking the length of suture.
Figure 5:
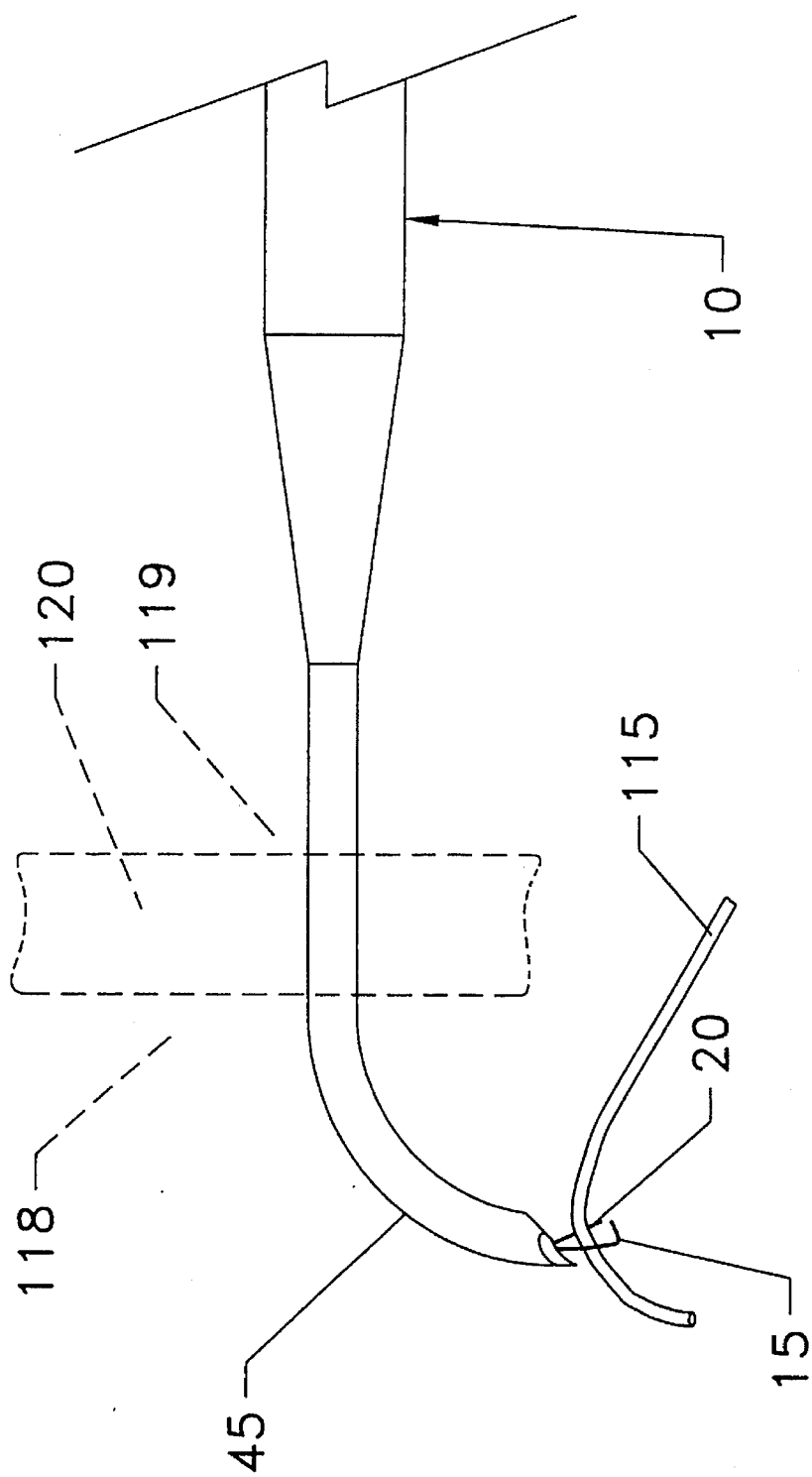
FIG. 5 is an illustrative side view similar to that of FIG. 4, except that the two wire-like elements have been partially retracted into the distal portion of the shaft so as to snare the suture.
Figure 6:
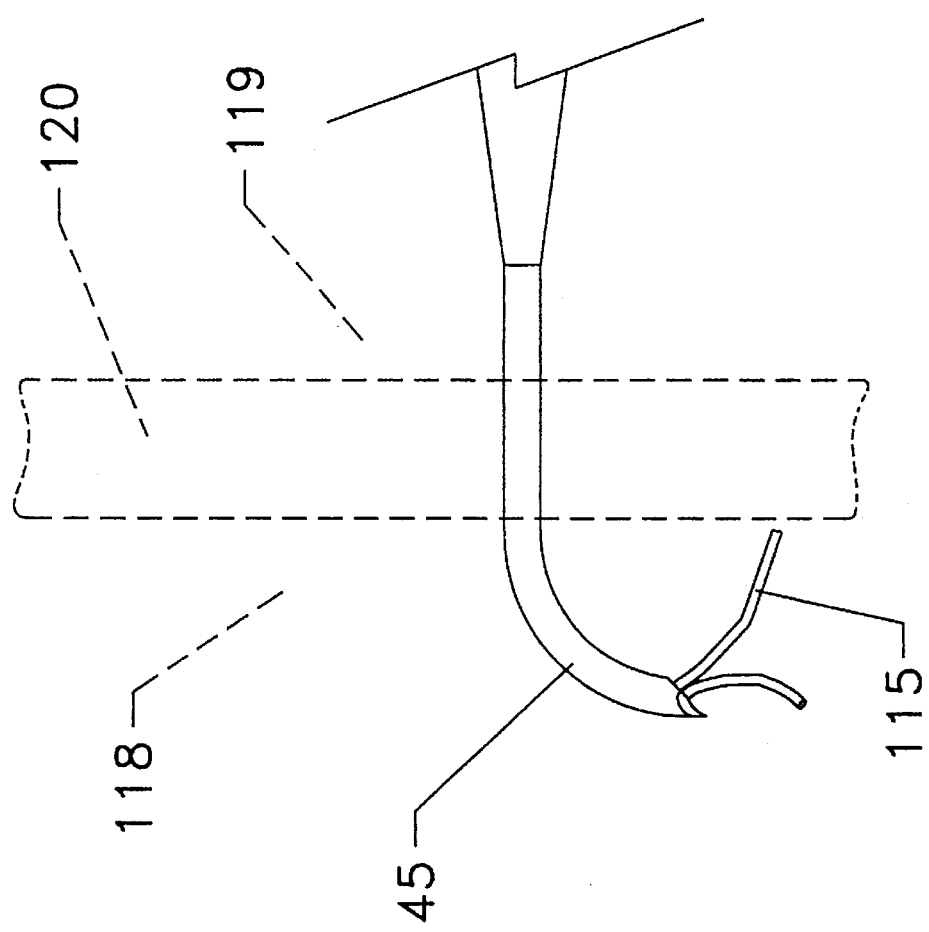
FIG. 6 is an illustrative side view similar to that of FIG. 5, except that the two wire-like elements have been fully retracted into the distal portion of the shaft so as to grasp the suture to the distal portion of the shaft.

First and second wire-like elements 15 and 20 each have a proximal end 65, 70 and a distal end 75, 80, respectively (see FIG. 4). Proximal ends 65 and 70 of wire-like elements 15 and 20 are attached to distal end 60 of rod 12, whereby wire-like elements 15 and 20 move in conjunction with rod 12. In addition, at least the distal ends 75 and 80 of the respective wire-like elements 15 and 20 normally bend or flare away from each other. Furthermore, the first wire-like element 15 is bent radially inwardly immediately adjacent to its distal end 75 so as to form a substantially hook-shaped configuration, generally indicated at 85.

Figure 7:
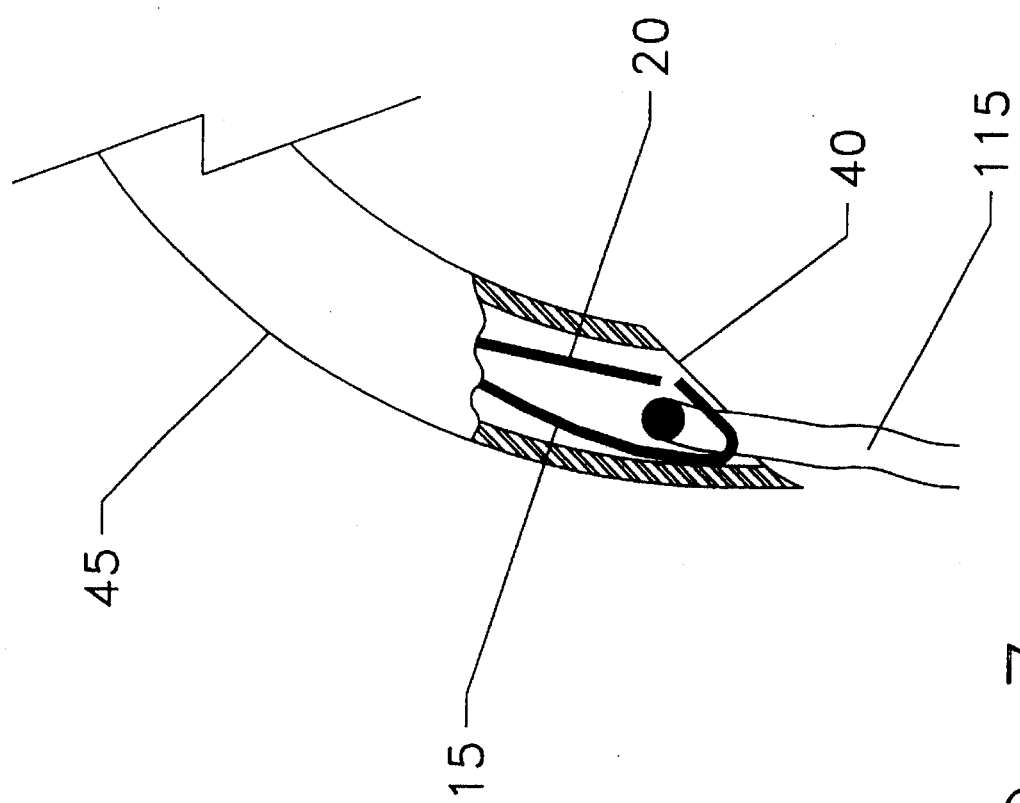
FIG. 7 is an illustrative side view, partially cut away and partially in section, showing the distal portion of the shaft of FIG. 6, with the two wire-like elements being retracted to their proximalmost position within the shaft and grasping a length of suture to the shaft.

The longitudinal lengths of first and second wire-like elements 15, 20 are selected such that when rod 12 is in its proximalmost position (FIG. 1), distal ends 75 and 80 of first and second wire-like elements 15 and 20 will be located within distal portion 45 of shaft 10. In this position, distal ends 75 and 80 of first and second wire-like elements 15 and 20 will be disposed in closely spaced relation to one another (see FIG. 7). When rod 12 is in its distalmost position (FIG. 2), however, distal ends 75 and 80 of first and second wire-like elements 15 and 20 will project outwardly from distal end 40 of shaft 10. In this position, distal ends 75 and 80 of first and second wire-like elements 15 and 20 flare outwardly away from one another (FIG. 4).

Actuation device 25 is attached to proximal end 30 of shaft 10 and to proximal end 55 of rod 12. In this embodiment, actuation device 25 includes a housing 90 attached to proximal end 30 of shaft 10. Housing 90 defines a cylindrical cavity 95 which is aligned with, and opens into, lumen 50 of shaft 10. A trigger 100 is pivotally attached to housing 90, and extends into cavity 95. A piston-like element 105 is securely attached to the proximal end 55 of rod 12, and is located in reciprocally sliding relation within the housing's cavity 95. A spring 110 biases piston-like element 105 proximally so that rod 12 will normally assume its aforementioned proximalmost position (FIG. 1). Piston-like element 105 may be moved distally against the force of spring 110 by trigger 100 so that rod 12 will assume it aforementioned distalmost position (FIG. 2).

It will, therefore, be understood that rod 12 normally resides in its proximalmost position (FIG. 1) and distal ends 75 and 80 of the two wire-like elements 15 and 20 normally reside within distal portion 45 of shaft 10. It is to be appreciated that when distal ends 75 and 80 of the two wire-like elements 15 and 20 reside within distal portion 45 of shaft 10, the pointed distal end 40 of shaft 10 may be forced through tissue without interference from distal ends 75 and 80 of wire-like elements 15 and 20 or from a length of suture which may be grasped thereby.

Device 5 may be used to grasp and manipulate a piece of suture 115 at a surgical site. Among other things, it may also be used to grasp a piece of suture 115 on either the left side 118 or the right side 119 of a tissue 120, and to pass that suture through the one or more layers making up tissue 120. The passage of suture 115 through tissue 120 may be accomplished either by pulling the suture through, or by pushing the suture through, tissue 120.

Figure 3:
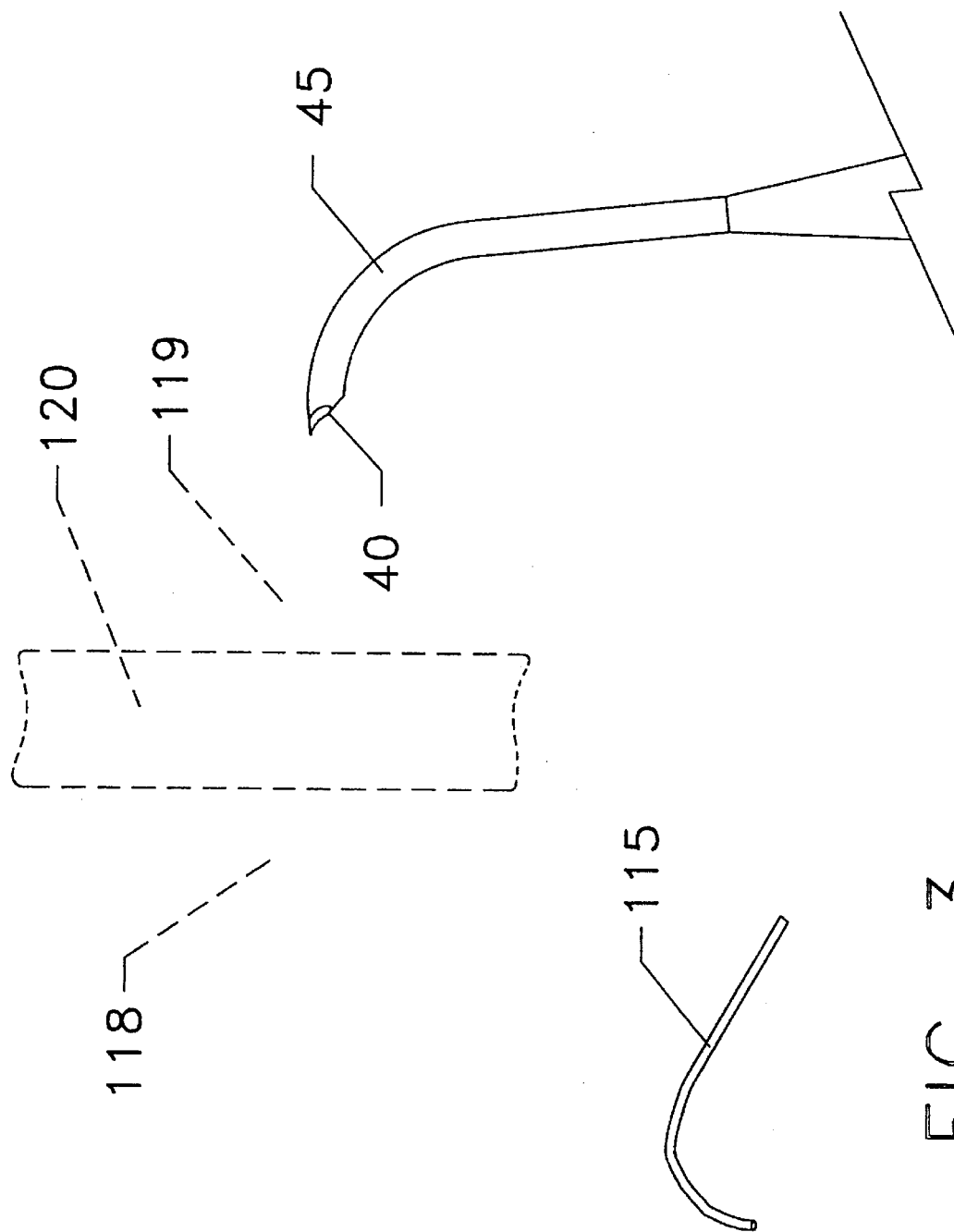
FIG. 3 is an illustrative side view, partially cut away, showing a piece of tissue in phantom, a length of suture and the distal portion of the shaft of a suture grasping device formed in accordance with the present invention, wherein the length of suture is located on one side of the tissue and the distal portion of the shaft is located on the other side of the tissue, and further wherein the two wire-like elements of the suture grasping device are shown in their retracted position.

More particularly, in those cases where it is desired to pull suture 115 through tissue 120 from tissue side 118 to tissue side 119, the steps of the method are illustratively shown in FIGS. 3 through 10. Starting from the position where suture 115 is located on tissue side 118 and distal end 40 of shaft 10 is located on tissue side 119 as shown in FIG. 3, the pointed distal end 40 of shaft 10 is first forced through tissue 120. Then shaft 10 is manipulated so as to bring its distal end 40 substantially adjacent to the portion of suture 115 which is to be carried back through tissue 120. Next, trigger 100 is activated so as to move rod 12 toward its distalmost position. This causes the distal ends 75, 80 of wire-like elements 15, 20 to extend out of distal end 40 of shaft 10 so that the wire-like elements flare away from each other. Device 5 is then manipulated further as needed so as to position suture 115 in the gap 121 formed between distal ends 75, 80 of first and second wire-like elements 15, 20 (see FIG. 4).

Trigger 100 is then released so as to allow rod 12 to move toward its proximalmost position under the influence of the spring 110. As this occurs, distal ends 75, 80 of the wire-like elements 15, 20 retreat back into distal portion 45 of shaft 10, and the wire-like elements 15, 20 move back toward one another as they re-enter distal portion 45 of shaft 10. During this retraction of the wire-like elements, hook 85 adjacent distal end 75 of first wire-like element 15 grapples the portion of suture 115 which is located within the closing gap 121 (see FIG. 5) and carries it toward distal end 40 of shaft 10.

As hook 85 enters distal end 40 of shaft 10, a portion of suture 115 also is drawn into the distal end of the shaft. Suture 115 is held in this position by the spring-biased hook 85 acting in co-operation with the distal end of shaft 10 (see FIGS. 6 and 7).

Hook 85, shaft 10 and suture 115 may be sized so that the suture is tightly bound to the shaft. Alternatively, the hook, the shaft and the suture may be sized so that suture is free to slide transversely relative to hook 85 inside the distal portion of the shaft.

Figure 8:
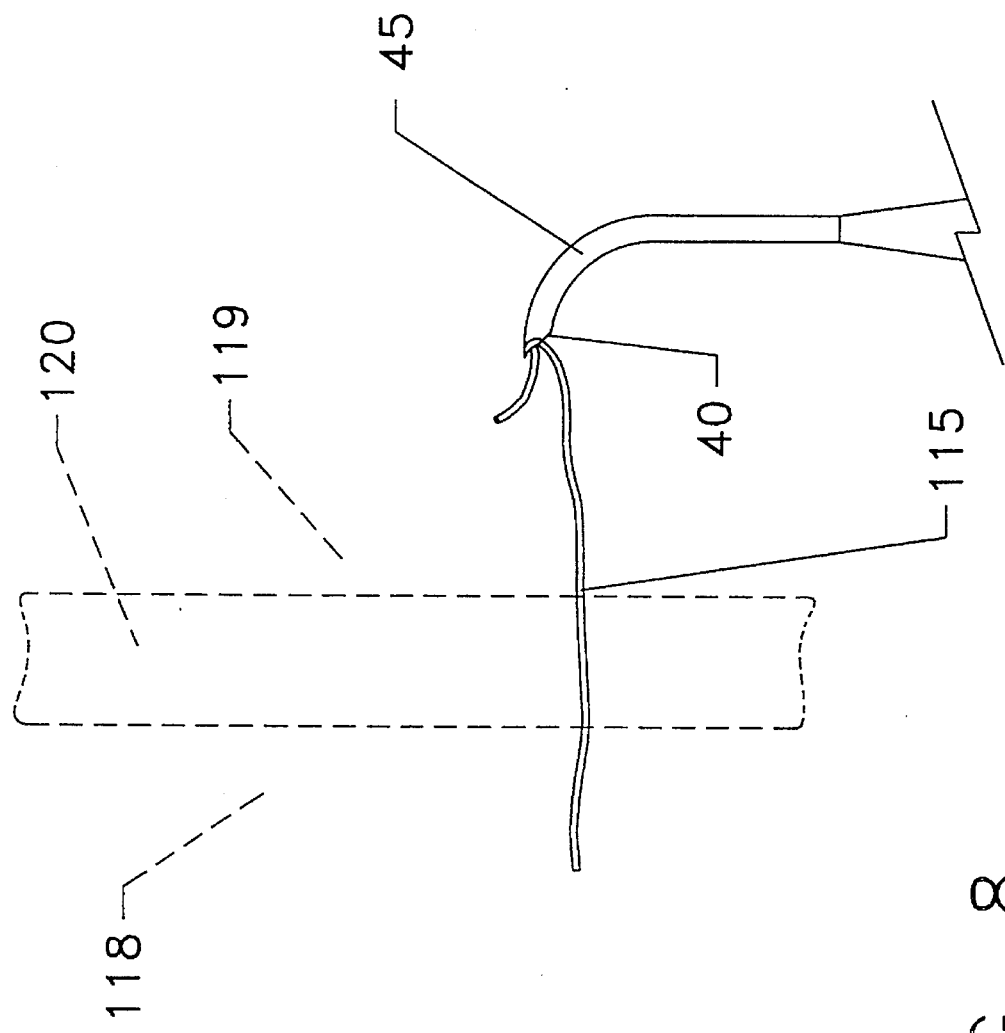
FIG. 8 is an illustrative side view similar to that of FIG. 6, except that the distal portion of the shaft has been withdrawn from the tissue.
Figure 9:
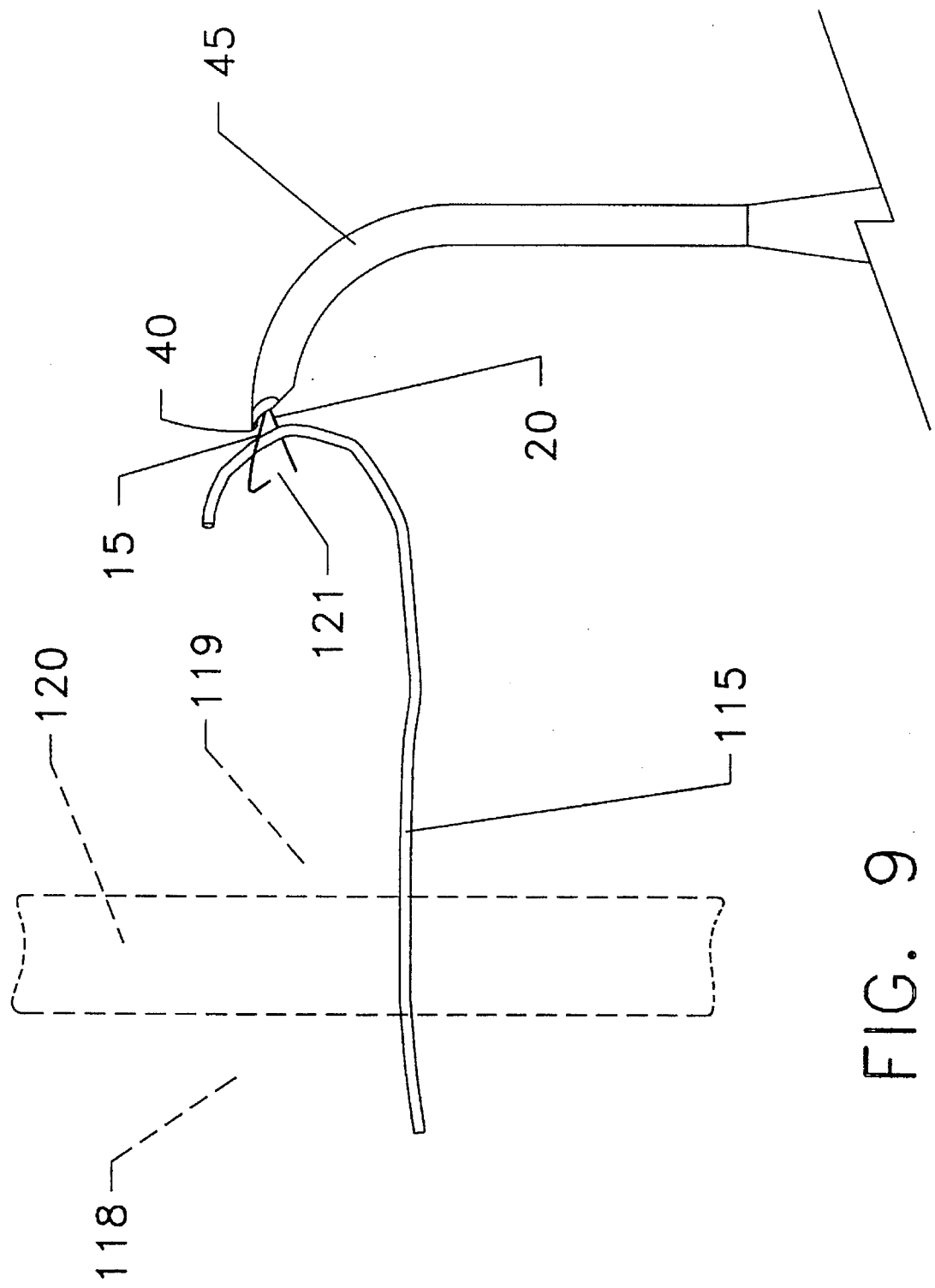
FIG. 9 is an illustrative side view similar to that of FIG. 8, except that the two wire-like elements are shown in their fully extended, flared position flanking the suture which has been drawn through the tissue.
Figure 10:
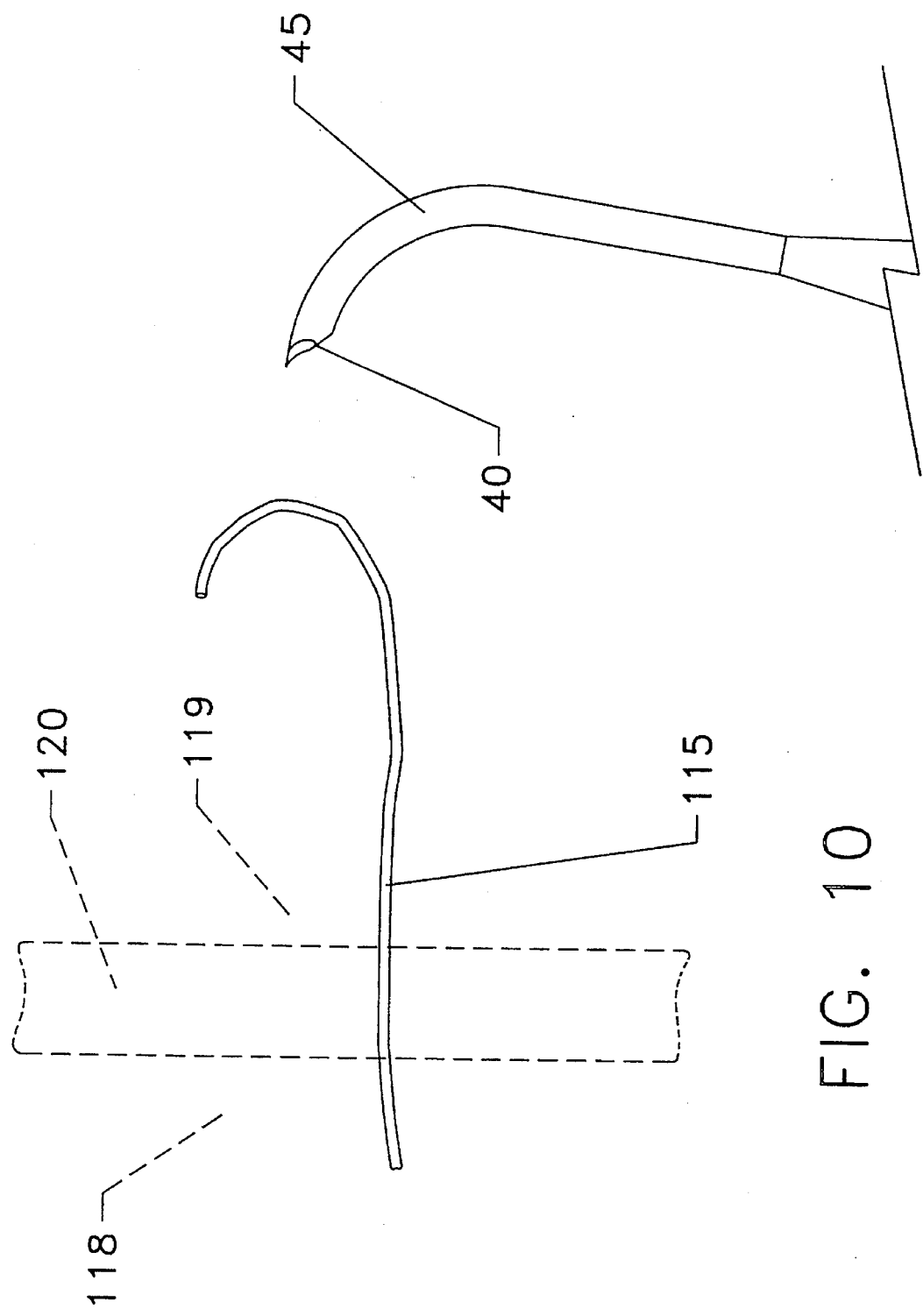
FIG. 10 is an illustrative side view similar to that of FIG. 9, except that the distal portion of the shaft is shown fully disengaged from the suture, with the two wire-like elements in their fully retracted position.
Figure 11:
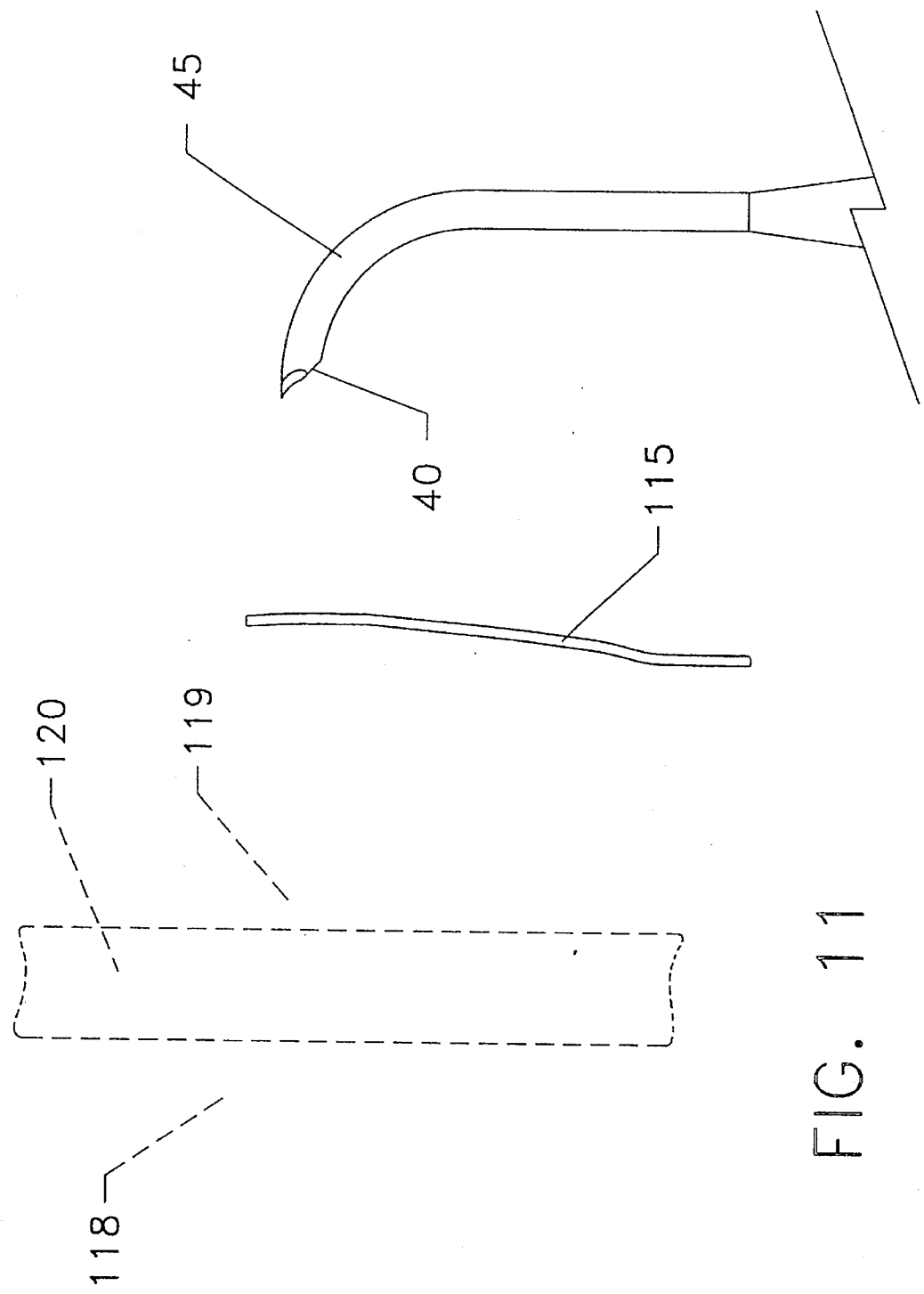
FIG. 11 is an illustrative side view, partially cut away, showing a piece of tissue in phantom, a length of suture and the distal portion of the shaft of a suture grasping device formed in accordance with the present invention, wherein the length of suture and the distal portion of the shaft are located on the same side of the tissue, and further wherein the two wire-like elements of the suture grasping device are shown in their retracted position.
Figure 12:
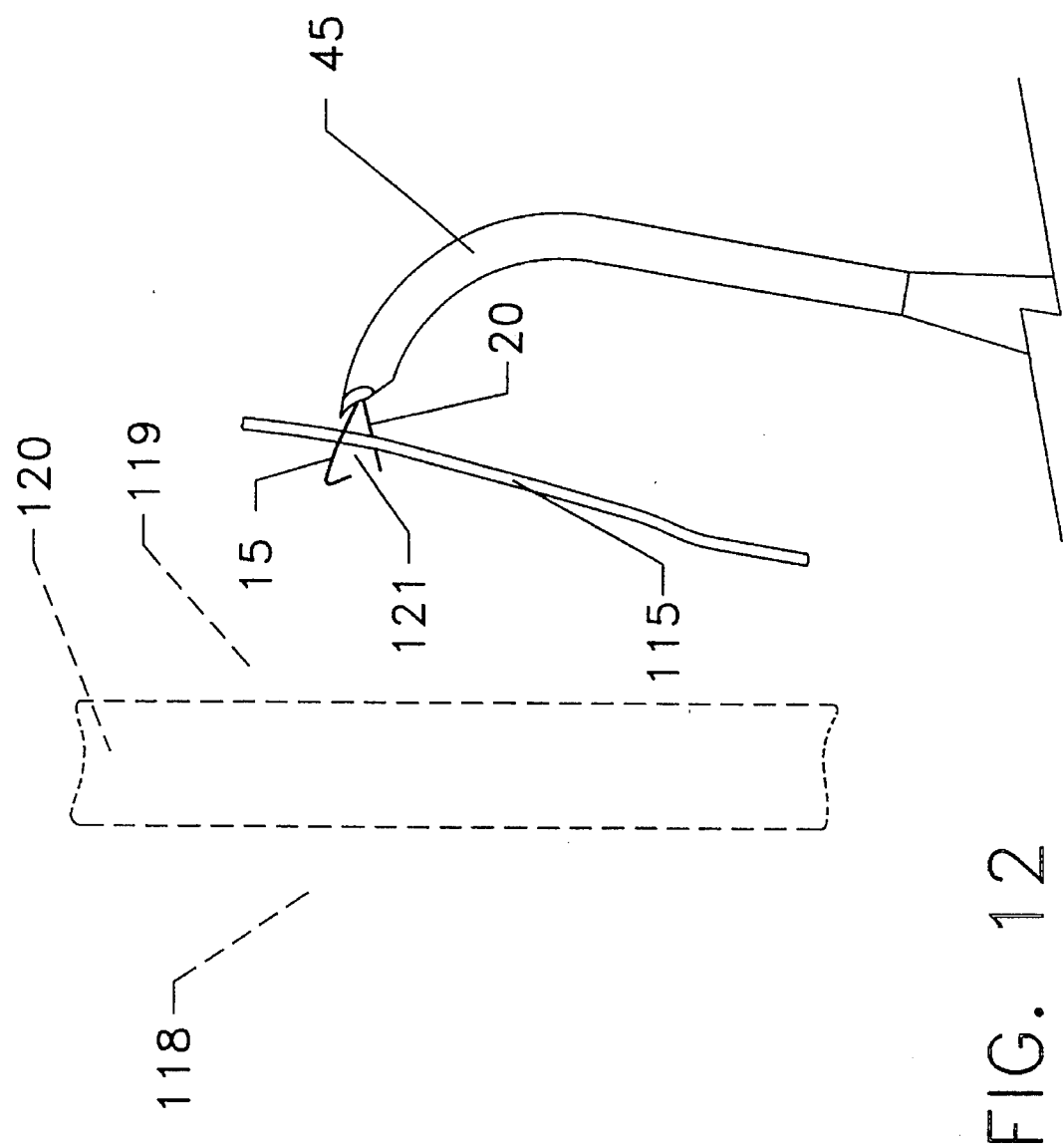
FIG. 12 is an illustrative side view similar to that of FIG. 11, except that the two wire-like elements are shown in their fully extended, flared positions flanking the length of suture.
Figure 13:
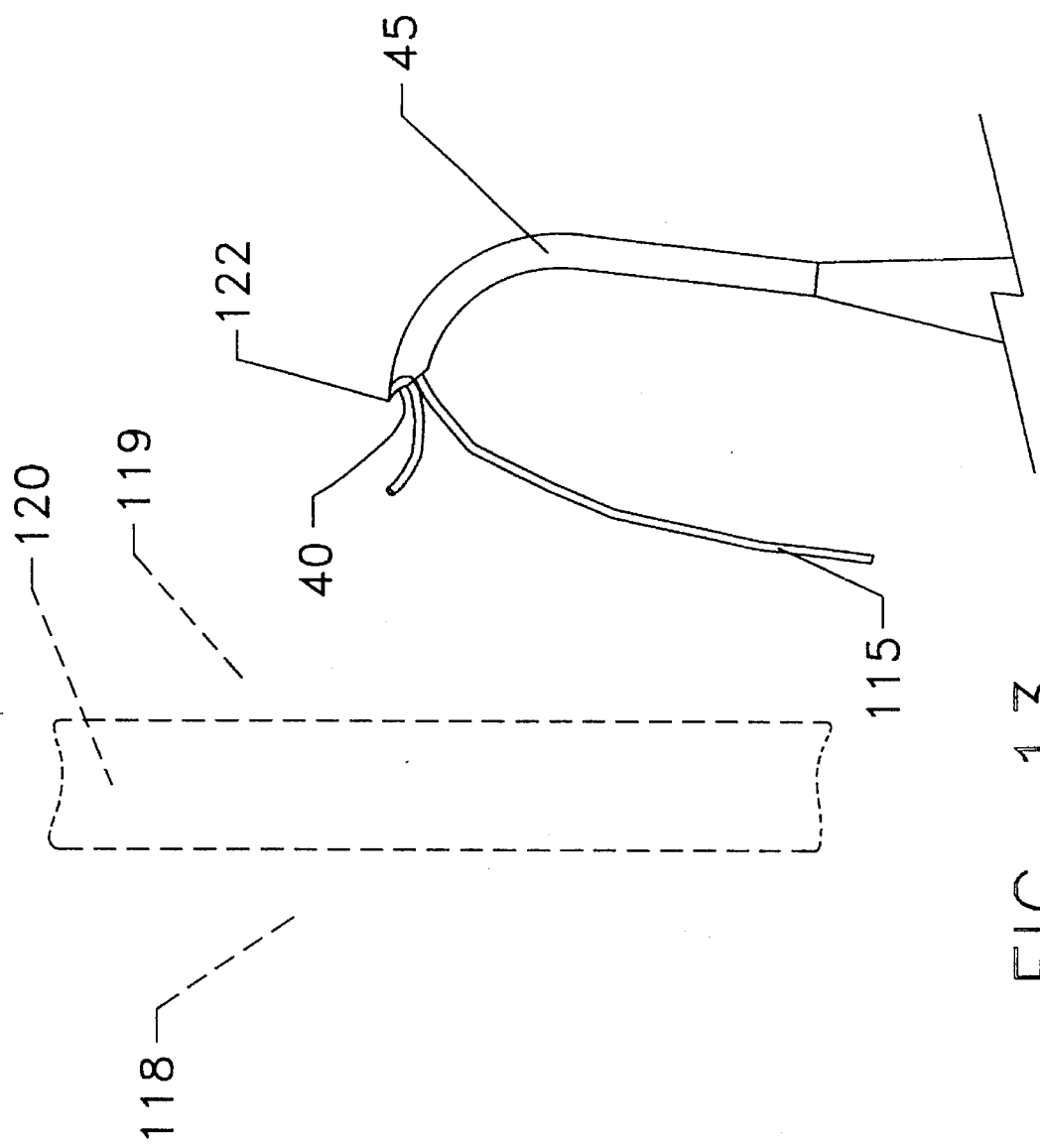
FIG. 13 is an illustrative side view similar to that of FIG. 12, except that the two wire-like elements have been fully retracted into the distal portion of the shaft so as to grasp the suture to the shaft.

Distal portion 45 of shaft 10 is then withdrawn from tissue 120, carrying the grappled suture 115 with it (see FIG. 8). Thereafter, suture 115 is released from device 5 by squeezing trigger 100 again. This causes wire-like elements 15, 20 to project outwardly from distal end 40 of shaft 10 in flaring relation to one another (see FIG. 9). Suture 115 then is released from tool 5 by manipulating the tool and/or the suture so that the suture no longer resides in gap 121 between distal ends 75, 80 of wire-like elements 15, 20 (see FIG. 10).

The procedure for pushing suture 115 through tissue 120 from tissue side 119 to tissue side 118 is somewhat similar in nature and is generally illustrated in FIGS. 11 through 16. Specifically, distal end 40 of shaft 10 is first positioned adjacent to suture 115 on tissue side 119 (see FIG. 11). Trigger 100 is then squeezed so as to project the wire-like elements 15, 20 outwardly from distal end 40 of shaft 10, in flaring relation to one another. Thereafter, device 5 is manipulated so that suture 115 resides in gap 121 between the distal ends of wire-like elements 15, 20 (see FIG. 12).

Trigger 100 is then released so as to allow the distal ends of wire-like elements 15, 20 to retract back into the distal portion of shaft 10 under the influence of spring 110. The distal ends of the two wire-like elements 15, 20 to move back toward one another as they re-enter distal portion 45 of shaft 10, closing down gap 121. As this occurs, hook 85 grapples suture 115 and draws the grappled portion against distal portion 45 of shaft 10. The engagement of suture 115 with distal end 40 of shaft 10 is such that the distalmost point 122 of distal end 40 is located distally of grasped suture 115 and wire-like elements 15, 20 (see FIG. 13).

Figure 14:
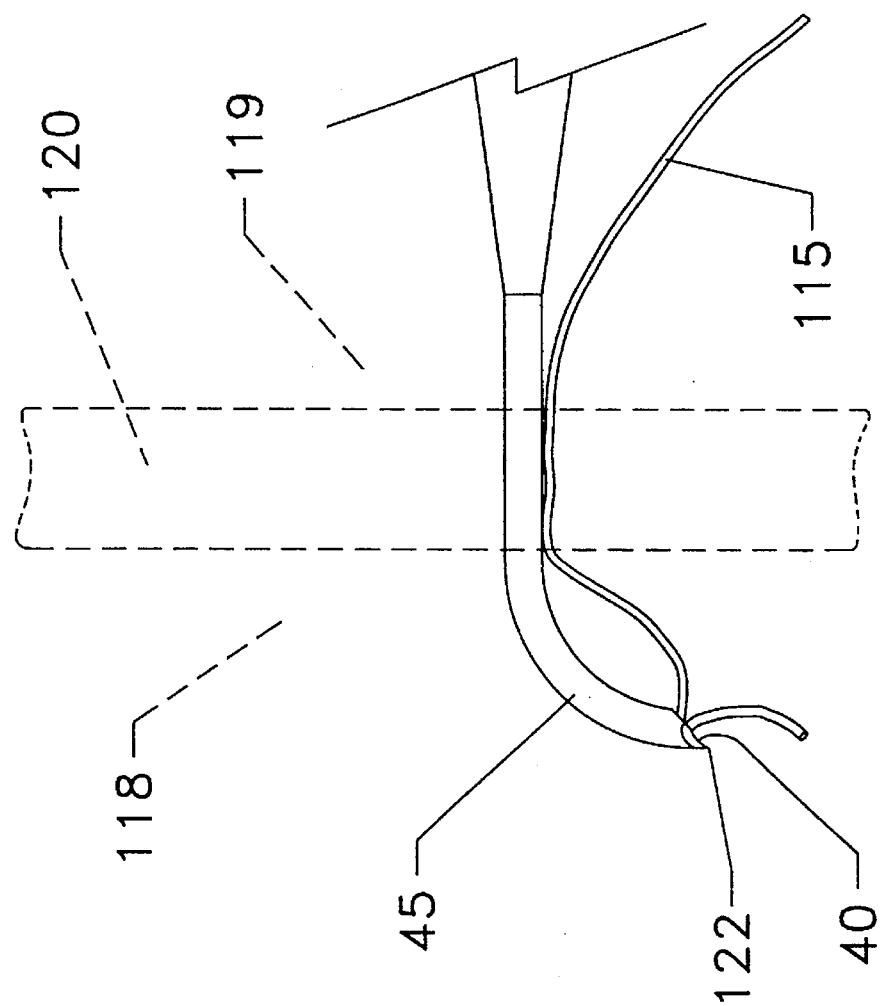
FIG. 14 is an illustrative side view similar to that of FIG. 13, except that the distal portion of the shaft has been forced through the tissue, carrying the suture with it.
Figure 15:
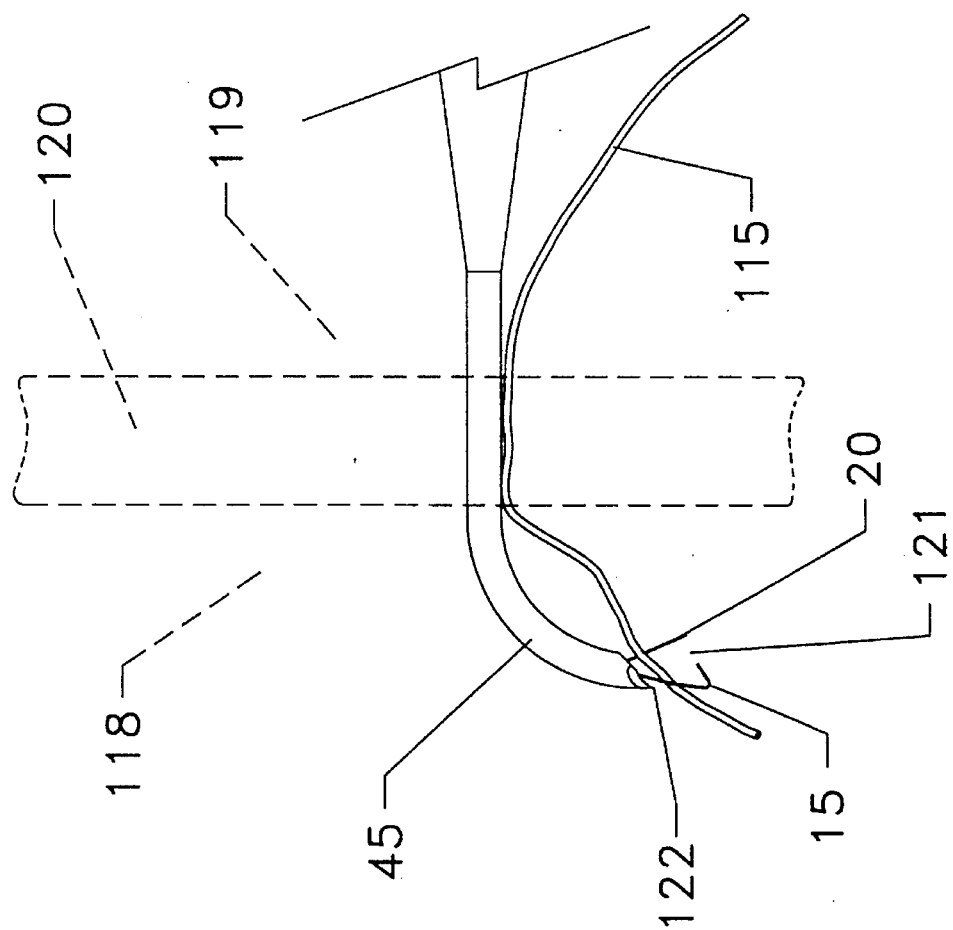
FIG. 15 is an illustrative side view similar to that of FIG. 14, except that the two wire-like elements have been positioned in their fully extended, flared positions flanking the suture.
Figure 16:
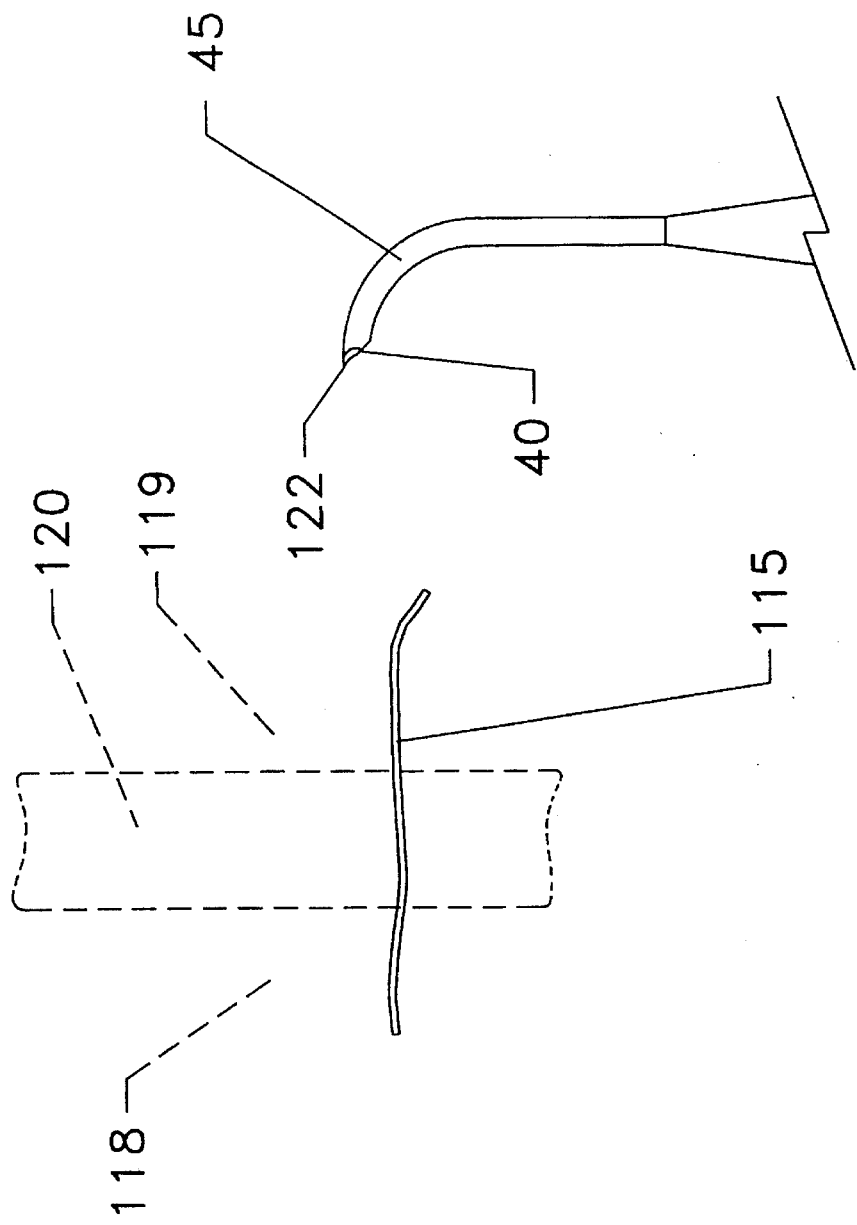
FIG. 16 is an illustrative side view similar to that of FIG. 15, except that the two wire-like elements have been fully retracted back into the distal portion of the shaft, and the shaft has been withdrawn from the tissue, leaving the length of suture extending through the tissue.

In this configuration, distal end 40 of shaft 10 is forced through tissue 120, carrying grappled suture 115 with it (see FIG. 14). Trigger 100 is then squeezed once again so as to project wire-like elements 15, 20 out of the distal end of shaft 10, in flaring relation to one another (see FIG. 15). Then tool 5 and/or suture 115 are manipulated so that suture 115 no longer sits in gap 121. This frees the suture from the tool. Then trigger 100 is released so as to retract wire-like elements 15 and 20 back into shaft 10. Shaft 10 is then withdrawn from tissue 120, leaving suture 115 extending through tissue 120 (see FIG. 16).

A suturing procedure requiring multiple passes of suture 115 through one or more layers of tissue also can be conveniently accomplished with device 5. For example, device 5 might be used to first pull a length of suture 115 through tissue 120, and thereafter to push that same suture 115 back through tissue 120 at a location adjacent to the first pass of the suture through the tissue. Alternatively, suture 115 could first be pushed through tissue 120, and thereafter pulled back through the tissue at a location adjacent to the first pass of the suture through the tissue.

Looking next at FIGS. 17–32, a representative suturing operation will be described for purposes of illustration.

Figure 17:
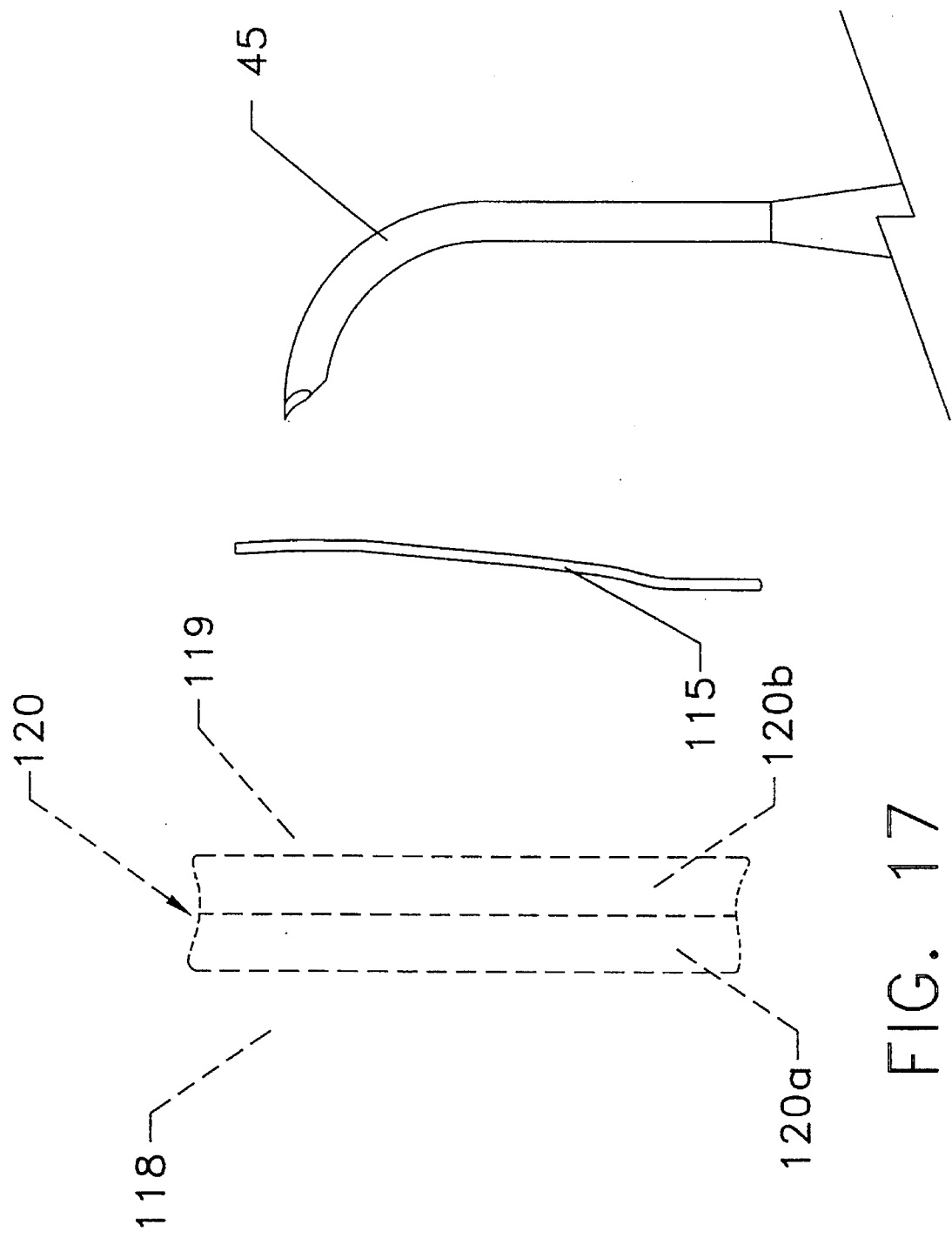
FIG. 17 is an Illustrative side view similar to that of FIG. 11, except that the tissue comprises two pieces of tissue in side-by-side relation to one another.
Figure 18:
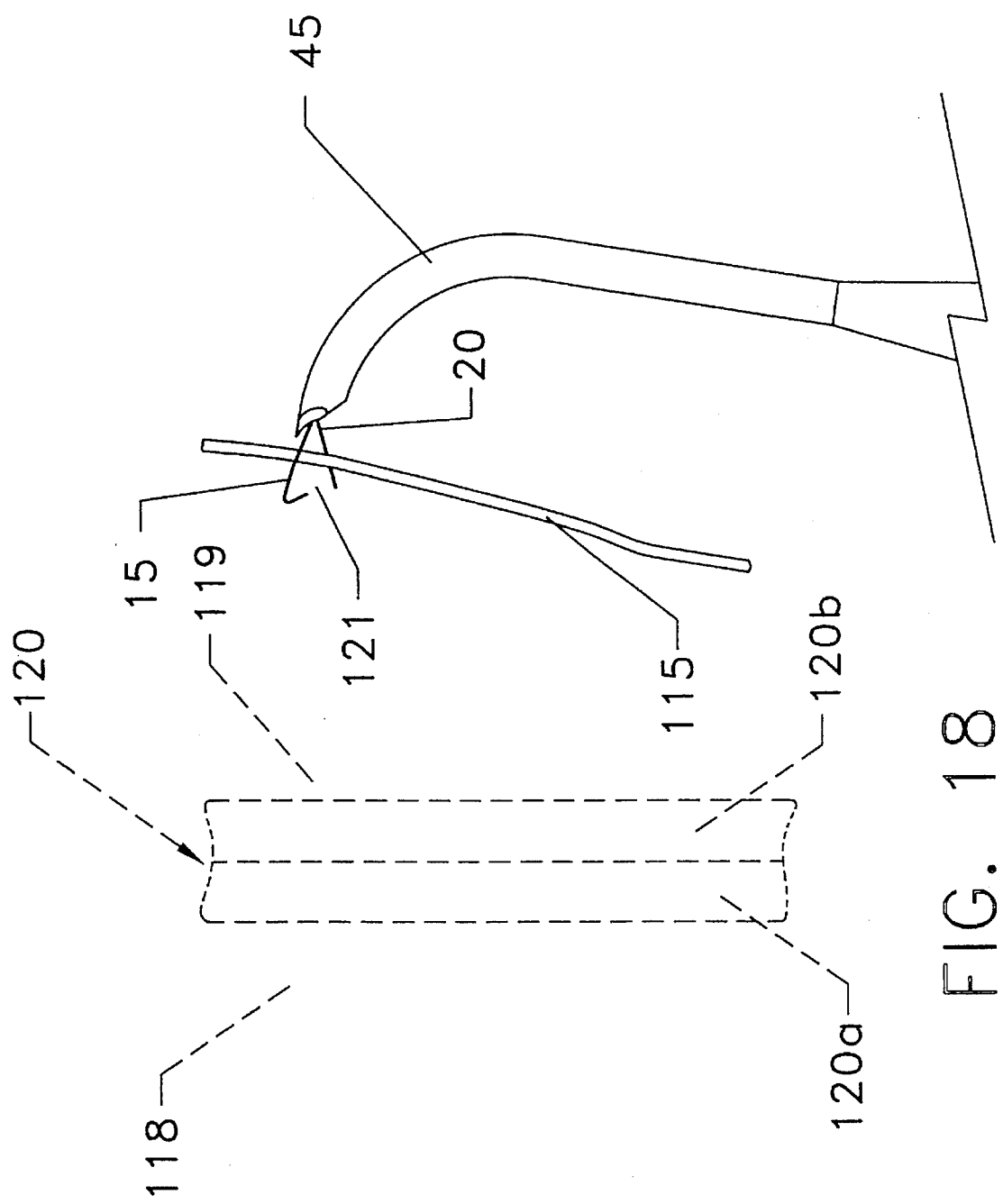
FIG. 18 is an Illustrative side view similar to that of FIG. 17, except that the two wire-like elements are shown in their fully extended, flared positions flanking the length of suture.
Figure 19:
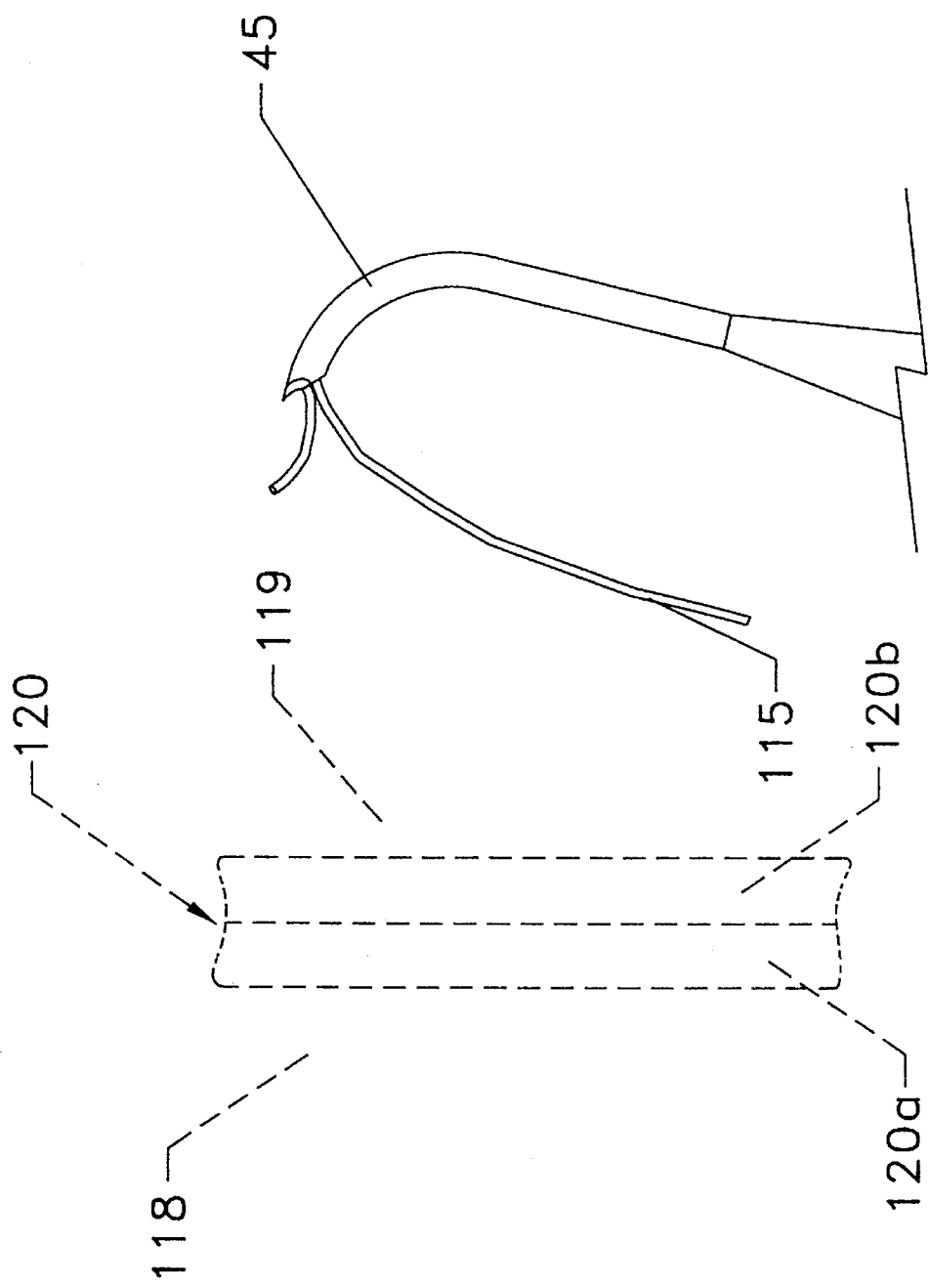
FIG. 19 is an illustrative side view similar to that of FIG. 18, except that the two wire-like elements have been fully retracted into the distal portion of the shaft so as to grasp the suture to the shaft.
Figure 20:
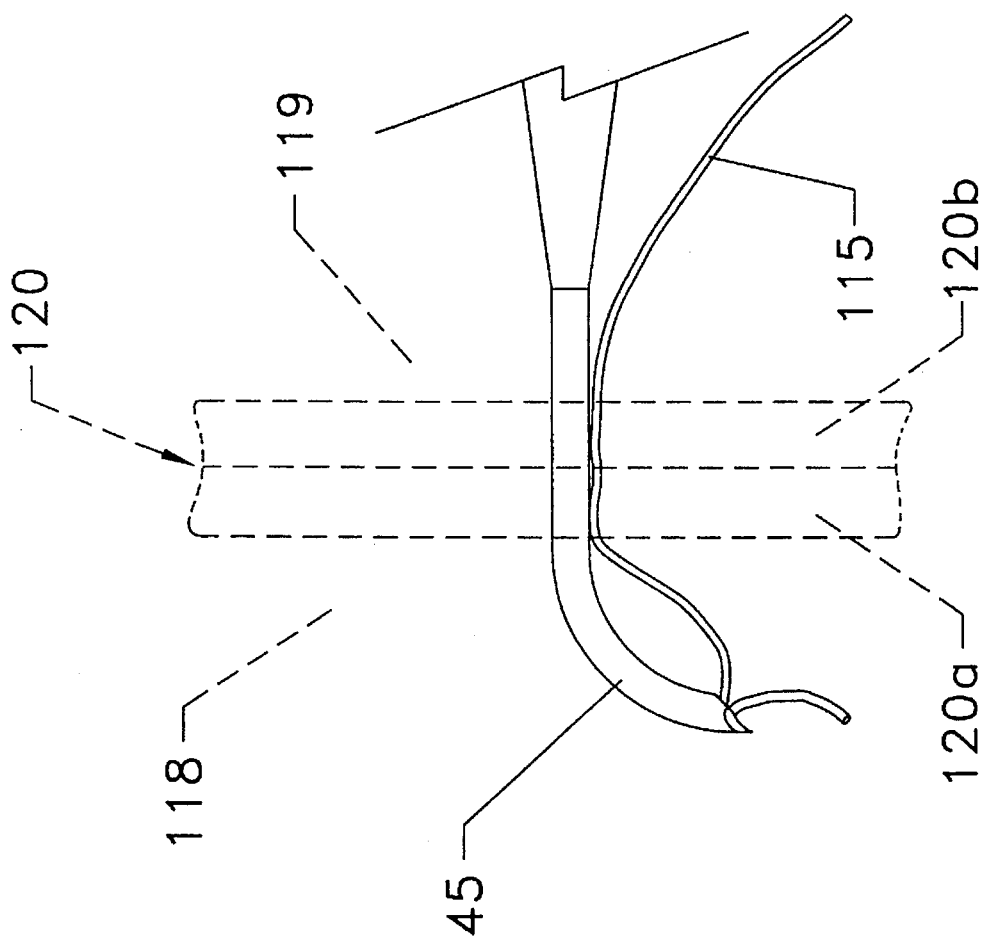
FIG. 20 is an illustrative side view similar to that of FIG. 19, except that the distal portion of the shaft has been forced through the tissue, carrying the suture with it.
Figure 21:
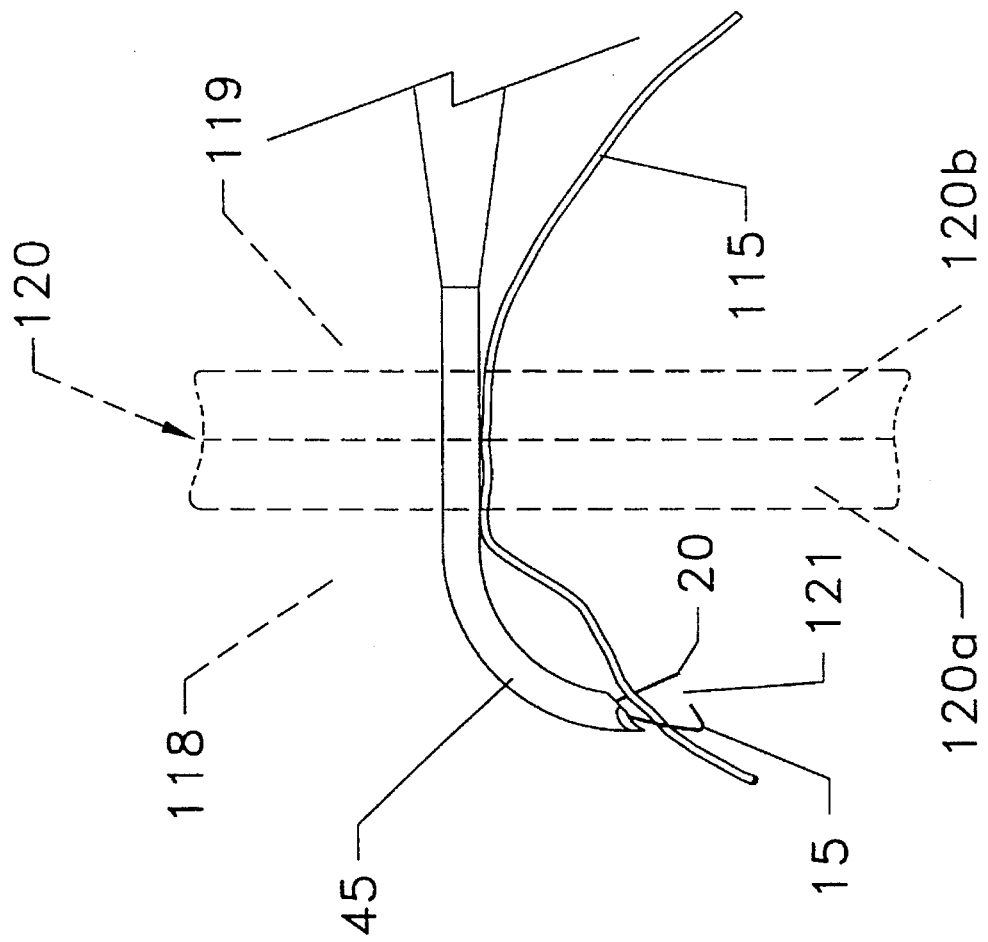
FIG. 21 is an illustrative side view similar to that of FIG. 20, except that the two wire-like elements have been positioned in their fully extended, flared positions flanking the suture.
Figure 22:
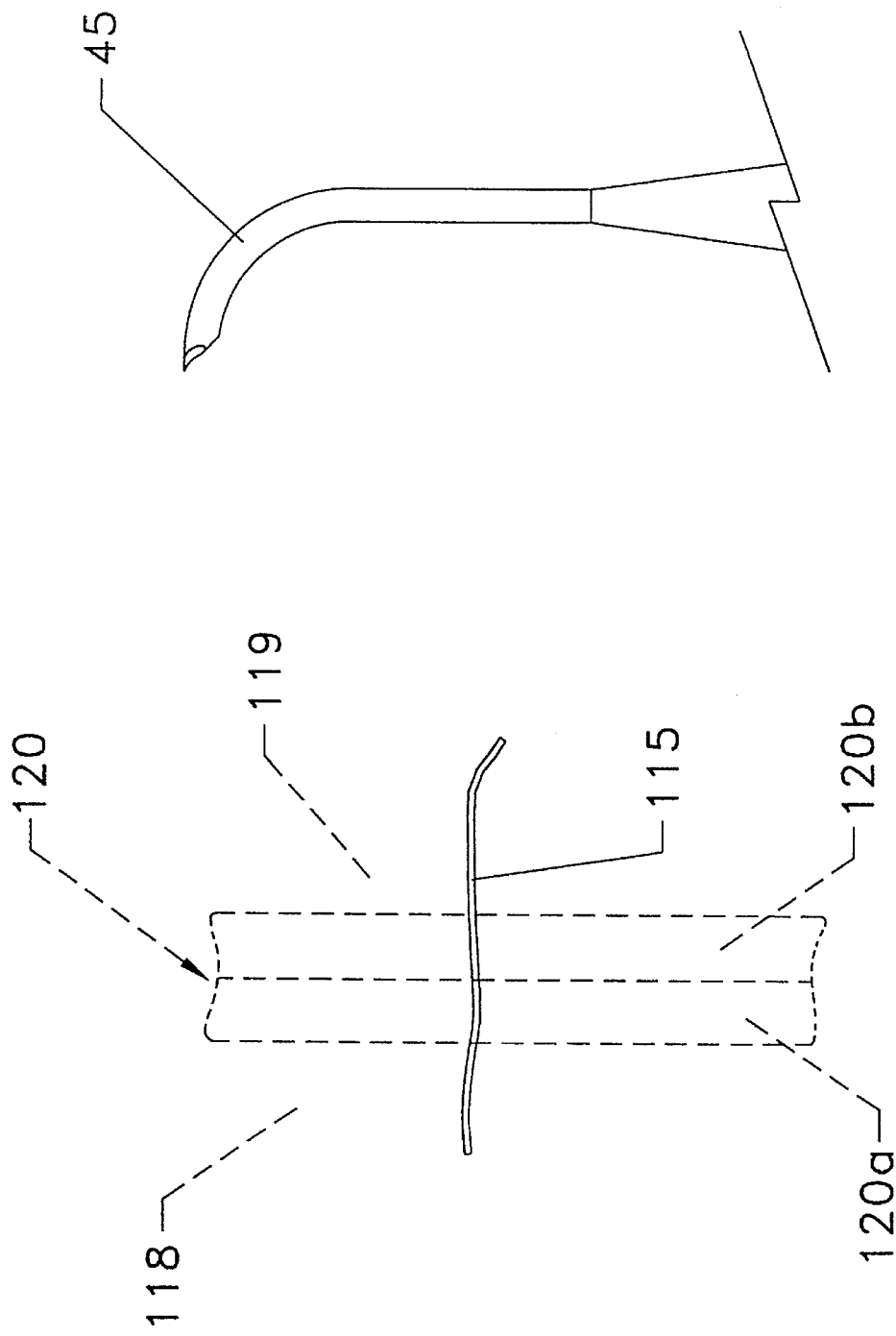
FIG. 22 is an illustrative side view similar to that of FIG. 21, except that the two wire-like elements have been fully retracted back into the distal portion of the shaft, and the shaft has been withdrawn from the tissue, leaving the length of suture extending through the tissue.
Figure 23:
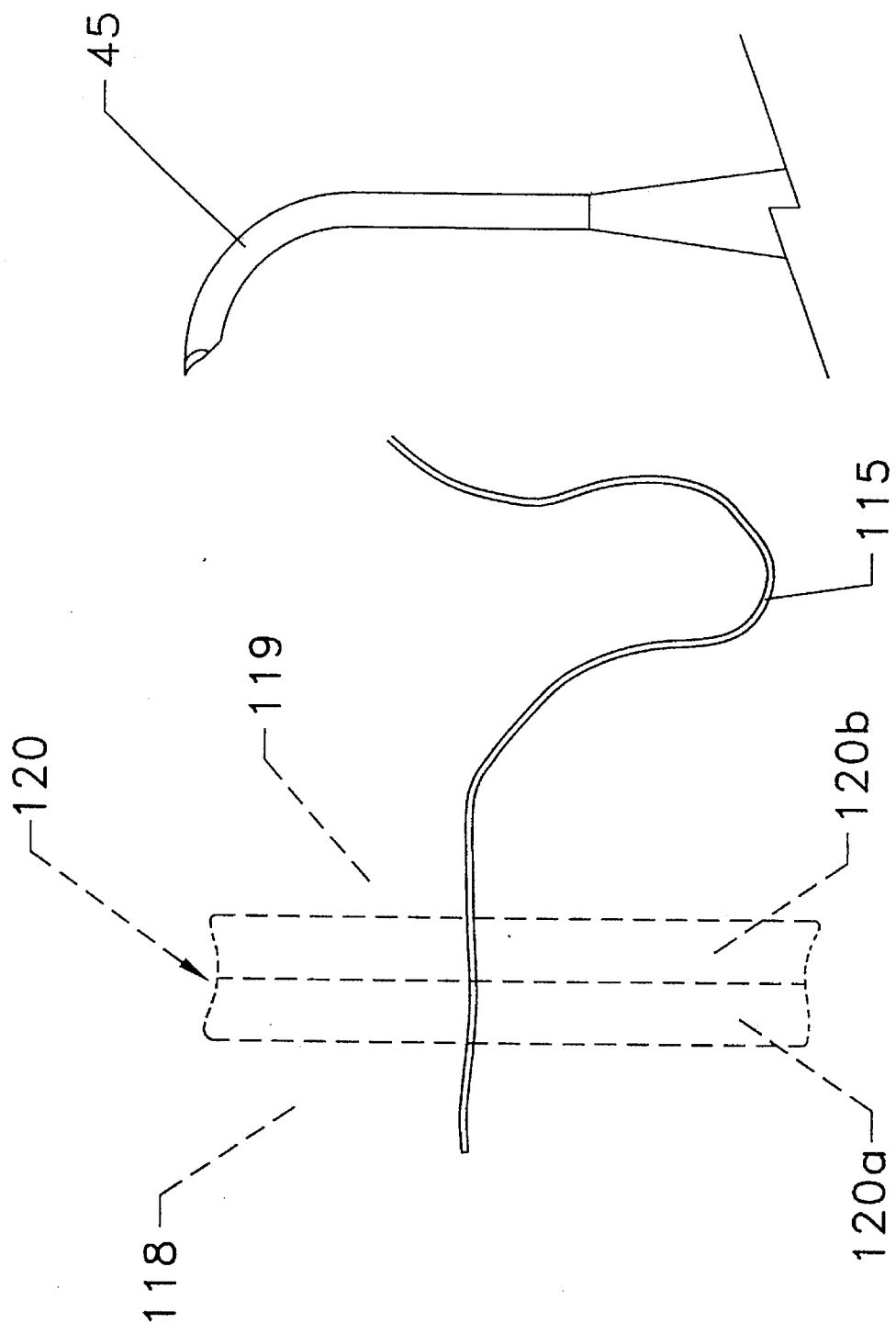
FIG. 23 is an illustrative side view similar to that of FIG. 22, except that an additional portion of the suture is shown.
Figure 24:
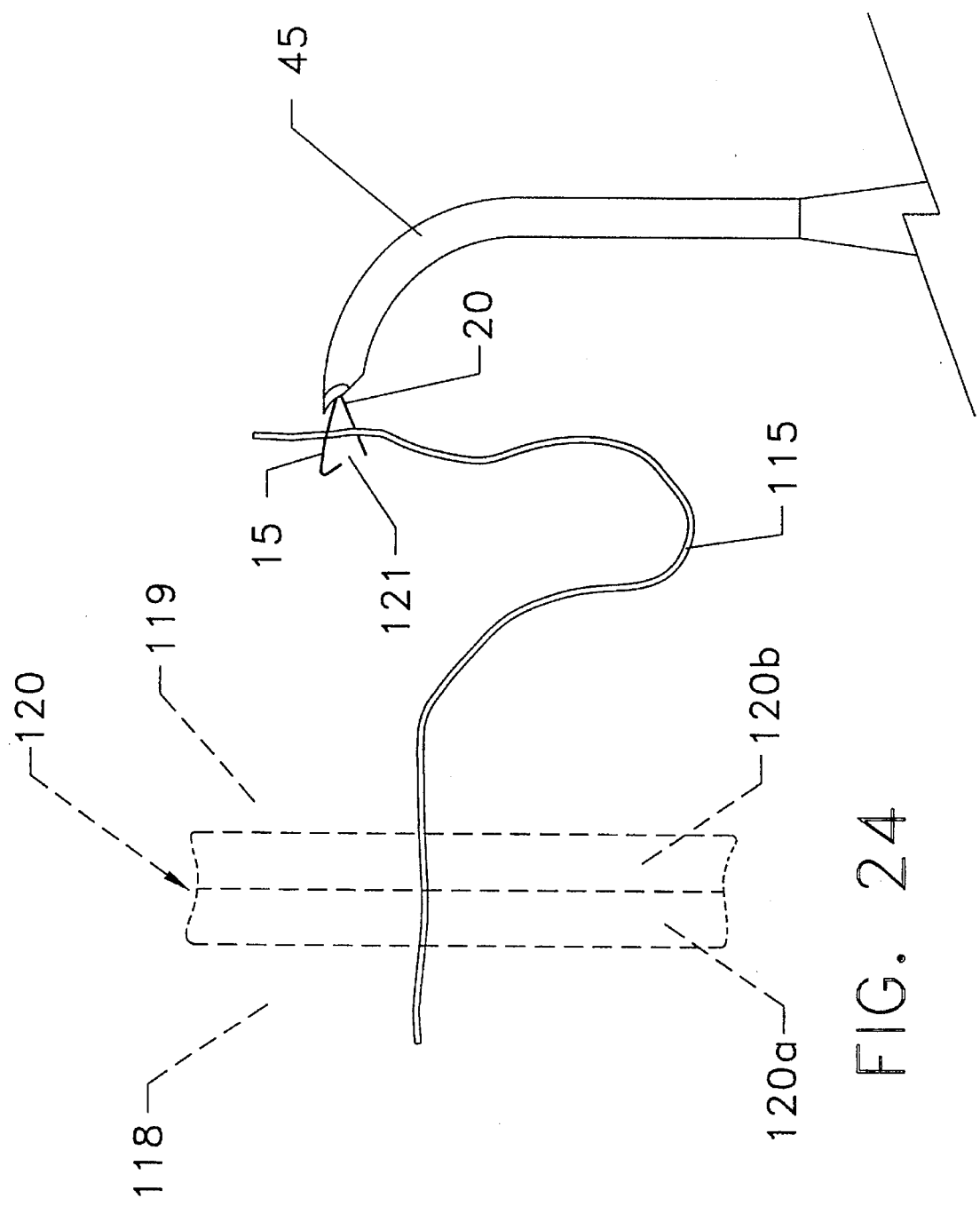
FIG. 24 is an illustrative side view similar to that of FIG. 23, except that the two wire-like elements have been extended to their fully extended, flared positions flanking a portion of the suture extending outwardly from the right hand side of the side-by-side pieces of tissue.
Figure 25:
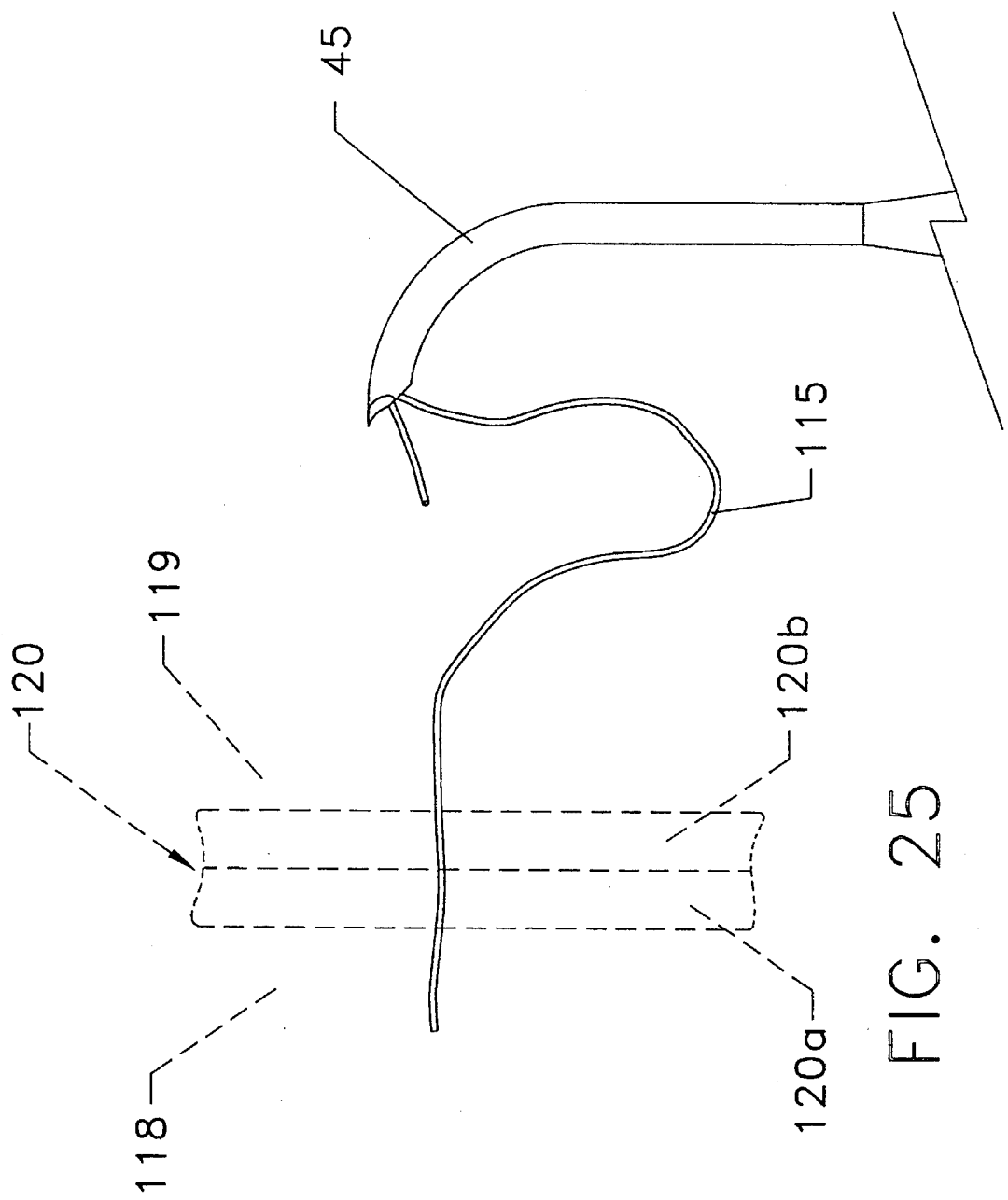
FIG. 25 is an illustrative side view similar to that of FIG. 24, except that the two wire-like elements have been fully retracted into the distal portion of the shaft so as to grasp the suture to the shaft.
Figure 26:
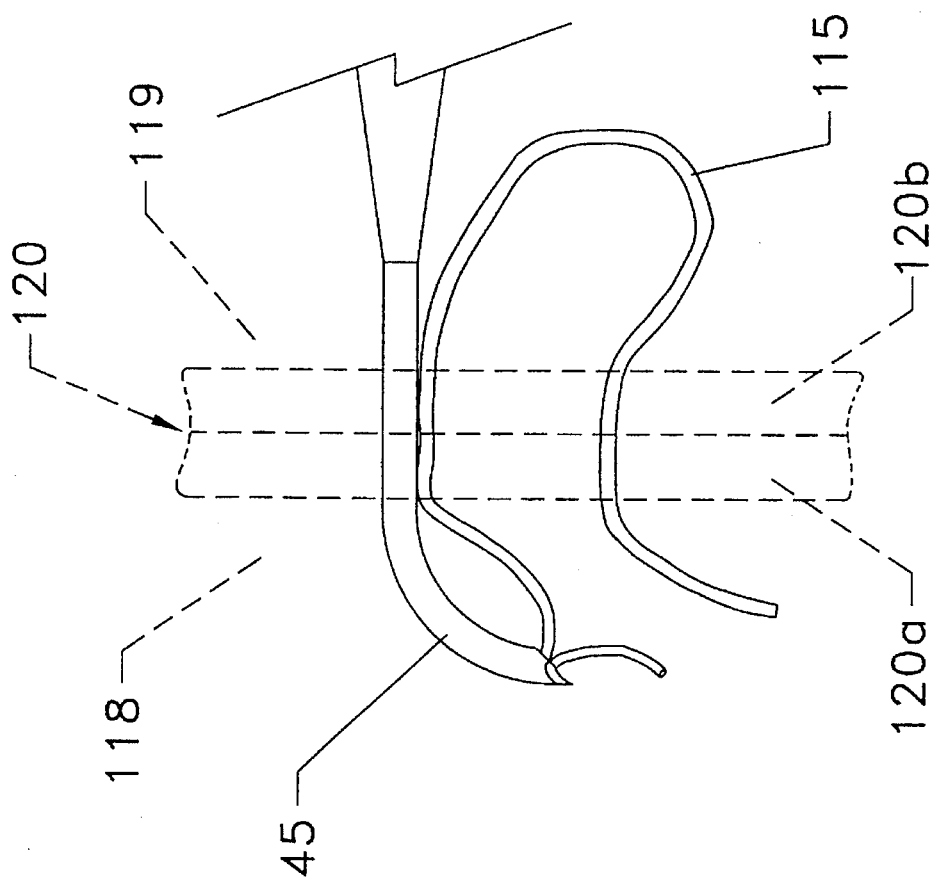
FIG. 26 is an illustrative side view similar to that of FIG. 25, except that the distal portion of the shaft has been forced through the tissue a second time, carrying the length of suture with it.
Figure 27:
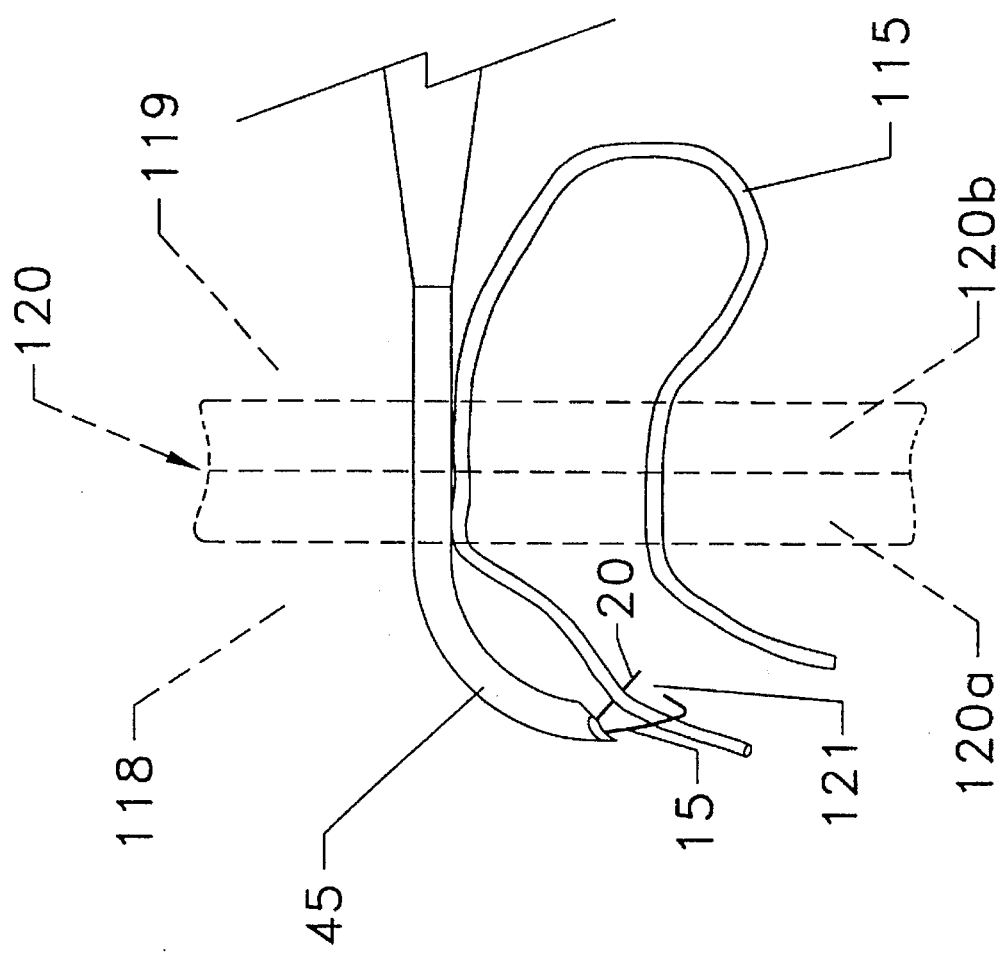
FIG. 27 is an illustrative side view similar to that of FIG. 26, except that the two wire-like elements have been positioned in their fully extended, flared positions flanking the suture.
Figure 28:
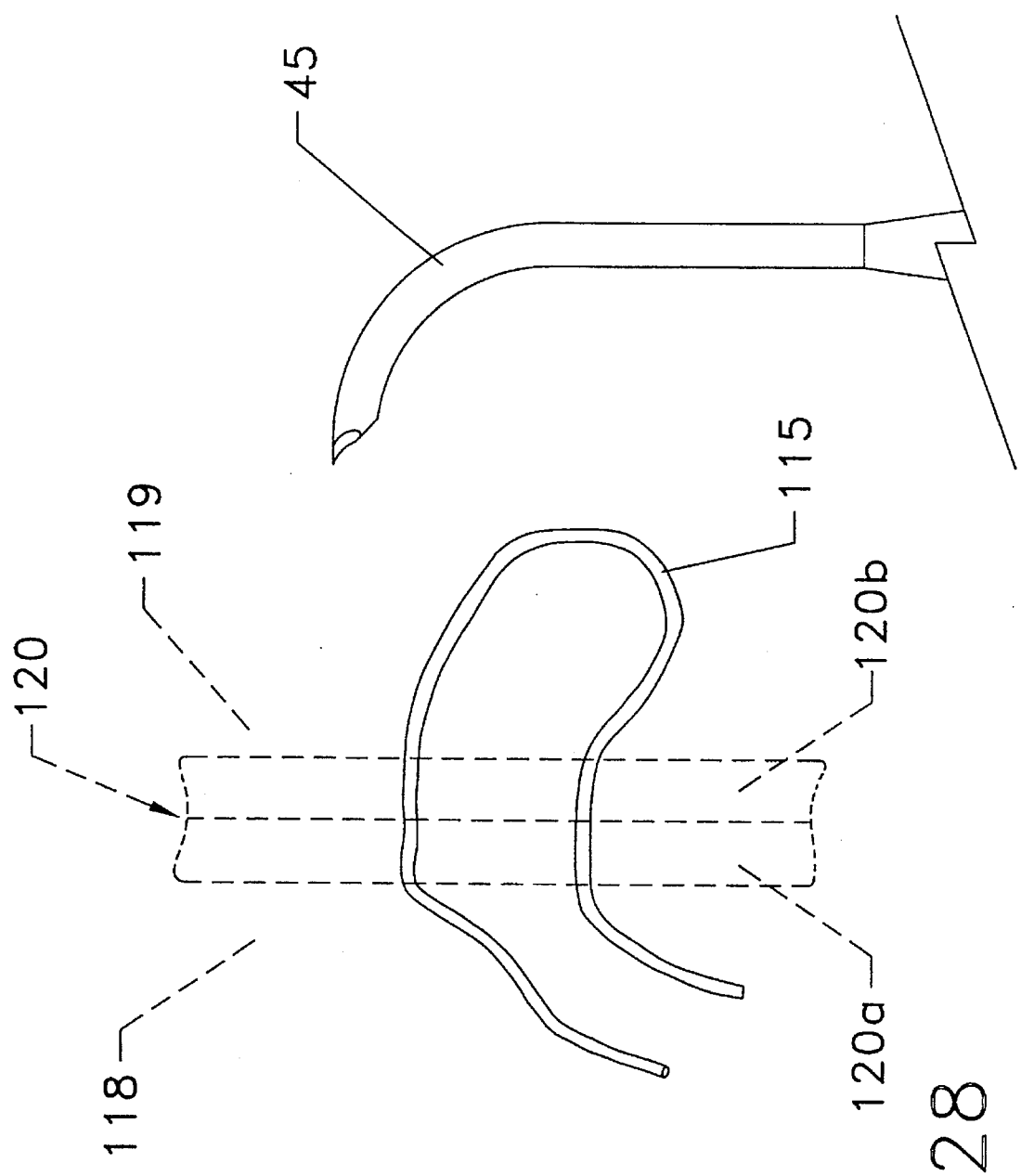
FIG. 28 is an illustrative side view similar to that of FIG. 27, except that the two wire-like elements have been retracted back into the distal portion of the shaft, and the shaft has been withdrawn from the tissue, so as to leave the length of suture extending from left to right through the tissue at a first location and extending from right to left through the tissue at a second location.
Figure 29:
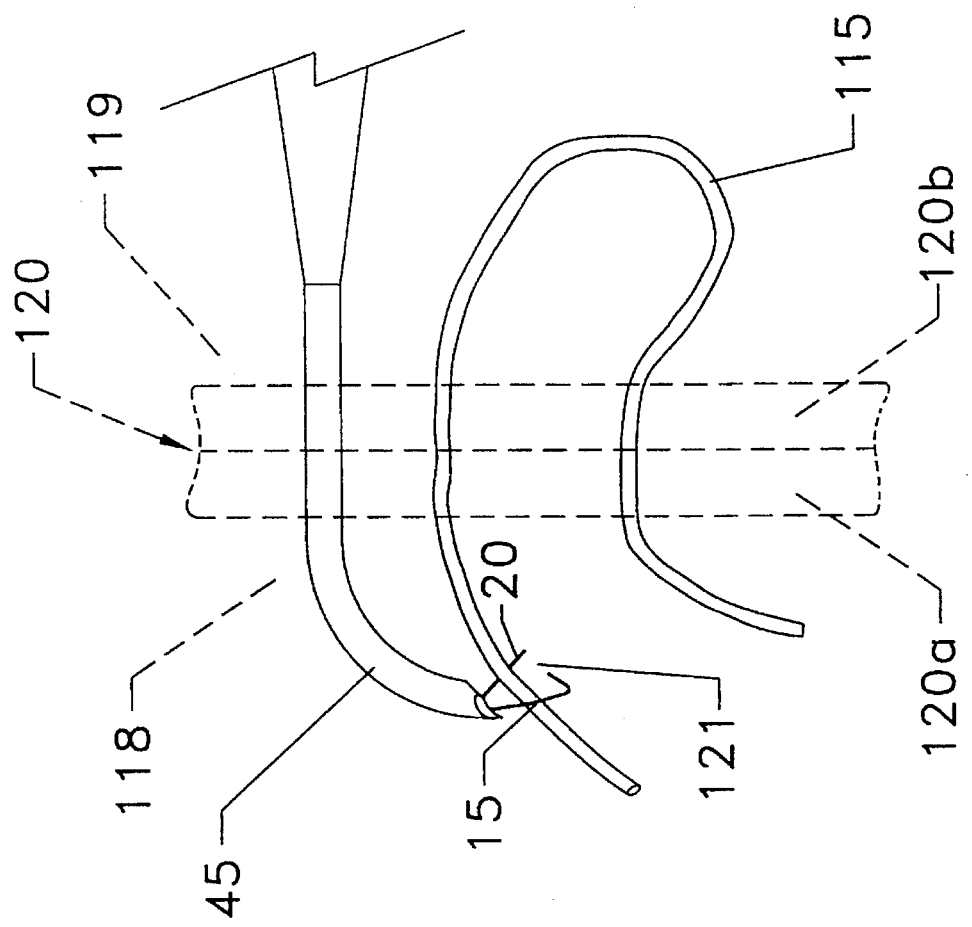
FIG. 29 is an illustrative side view similar to that of FIG. 28, except that the shaft extends left to right through the tissue at a third location, and wherein the two wire-like elements are located in their fully extended, flared positions flanking one of the free ends of the length of suture located on the left side of the tissue.
Figure 30:
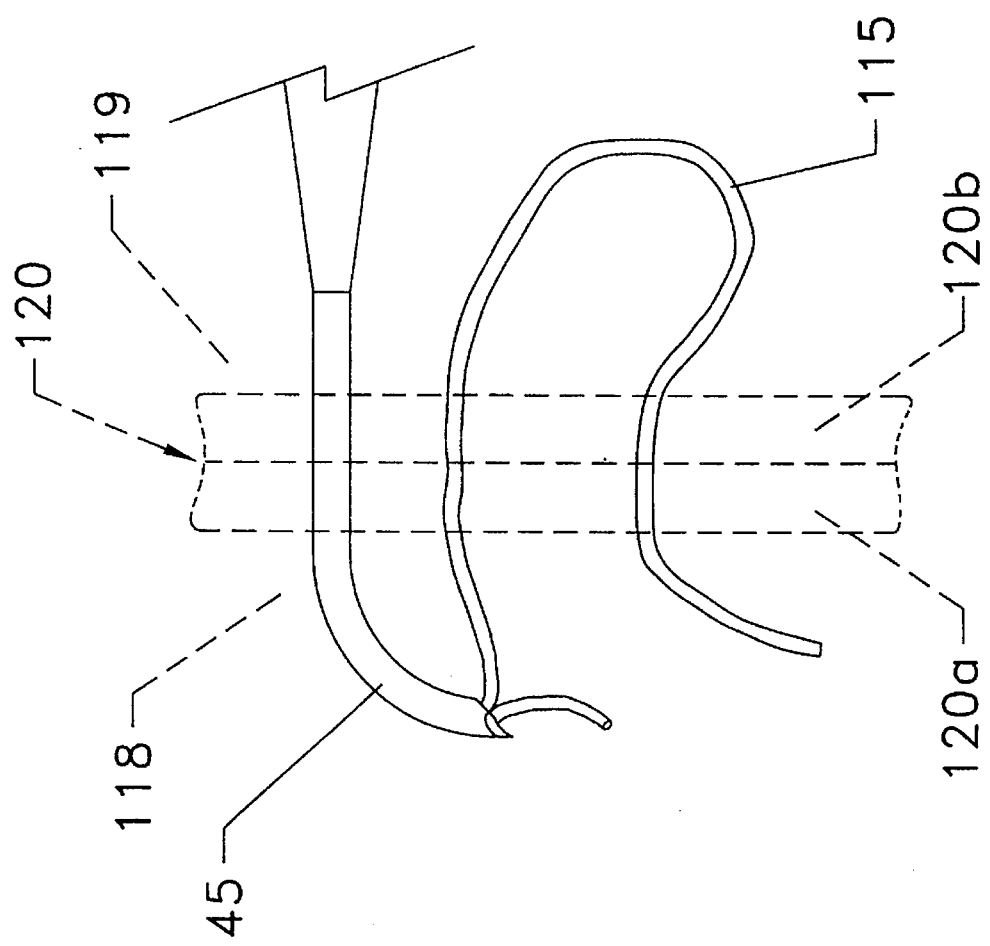
FIG. 30 is an illustrative side view similar to that of FIG. 29, except that the two wire-like elements have been moved to their fully retracted position so as to grasp one of the free ends of suture on the left side of the tissue to the shaft.
Figure 31:
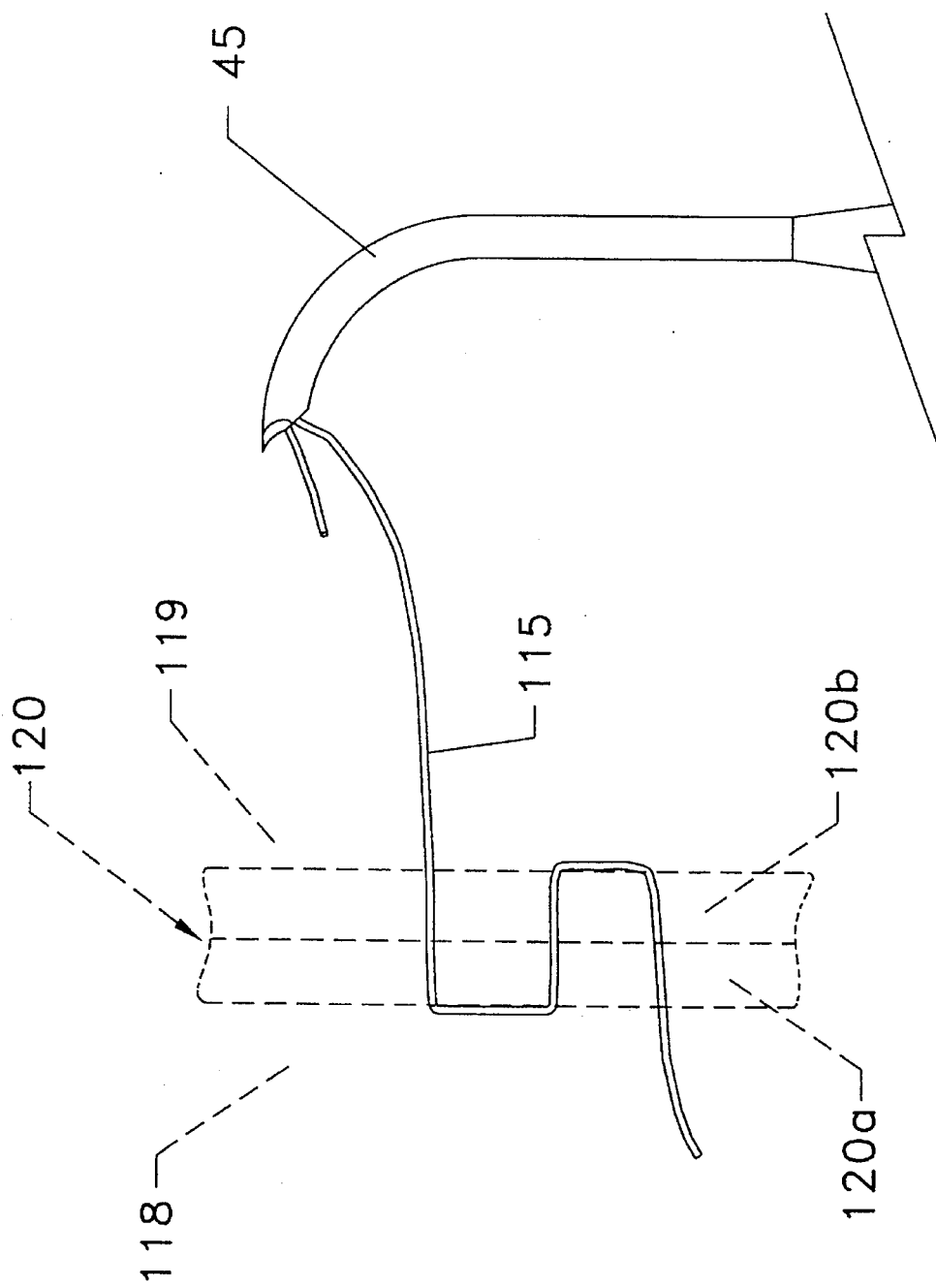
FIG. 31 is an illustrative side view similar to that of FIG. 30, except that the distal portion of the shaft has been withdrawn from the tissue, carrying a free end of the suture with it.
Figure 32:
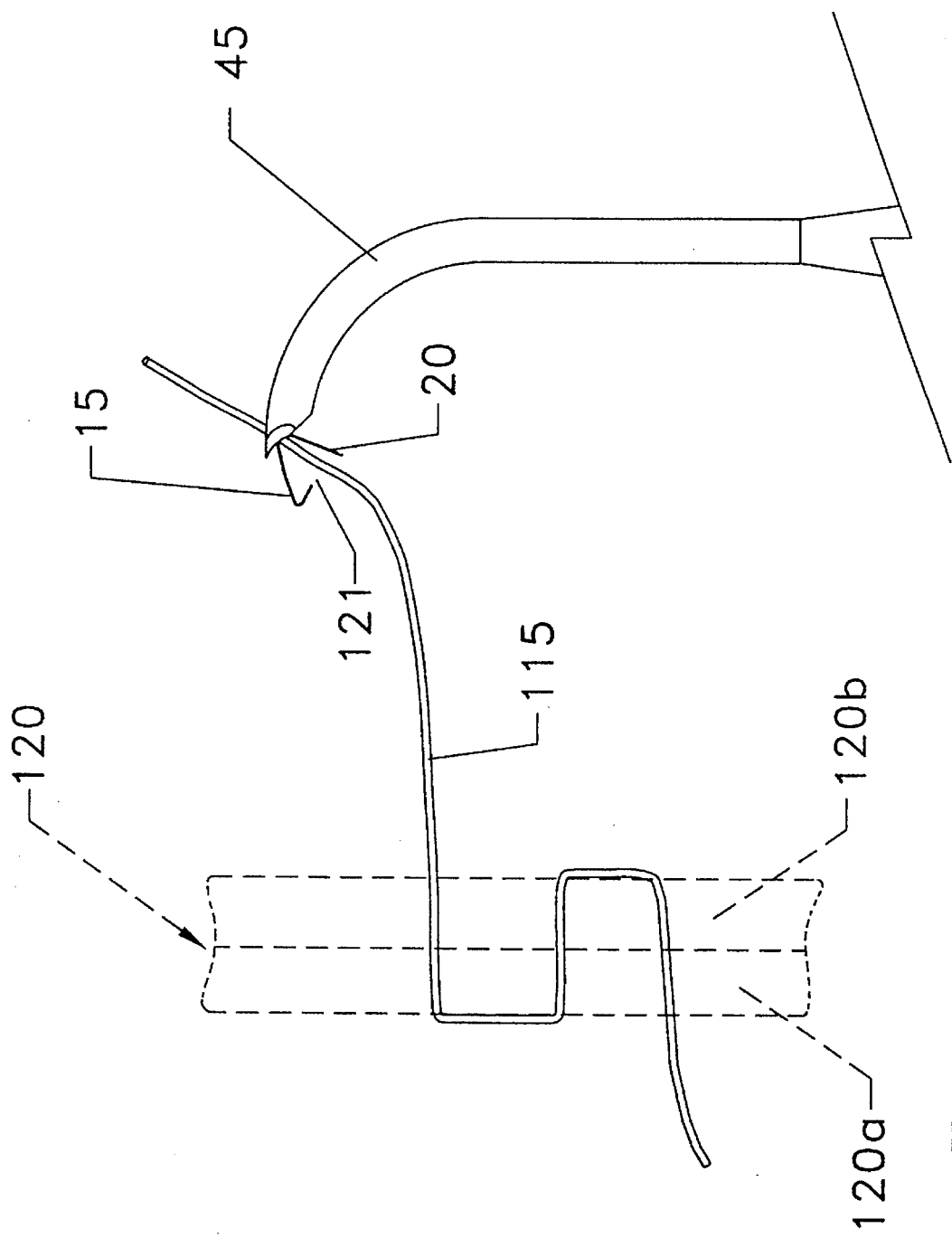
FIG. 32 is an illustrative side view similar to that of FIG. 31, except that the two wire-like elements have been positioned in their fully extended, flared positions flanking the length of suture.

FIG. 17 shows tissue 120, a length of suture 115 adjacent side 119 of tissue 120, and distal portion 45 of a device 5 formed in accordance with the present invention. Tissue 120 is shown as including layers 120a and 120b in abutting relationship to one another so as to represent the capability of device 5 to secure together multiple layers of tissue.

FIGS. 18–22 respectively show (i) engagement of wire-like elements 15, 20 with suture 115; (ii) grasping of suture 115 to distal end 40 of device 5; (iii) pushing the distal portion of shaft 10 through tissue 120, carrying suture 115 therewith; (iv) release of suture 115 from distal end 40 of shaft 10; and (v) disengagement of wire-like elements 15, 20 from suture 115 and withdrawal of distal portion 45 from tissue 120, leaving suture 115 extending therethrough. The details of this procedure are the same as those just described with respect to pushing a length of suture through tissue.

FIGS. 23–28 illustrate the use of the same procedure to pass the free end of suture 115 left adjacent to side 119 of tissue 120 back through tissue 120 at a location spaced from the first pass of the suture through tissue 120. Accordingly, it will be seen that in FIG. 28 both free ends of suture 115 have been pushed from tissue side 119 through tissue 120 to tissue side 118.

Finally, FIGS. 29–32 illustrate the use of the pulling technique described above to draw one of the free ends of suture 115 from tissue side 118 back through tissue 120 to tissue side 119. This third pass of suture through tissue 120 takes place at a location spaced from the first two passes of suture 115 through tissue 120.

Figure 33:
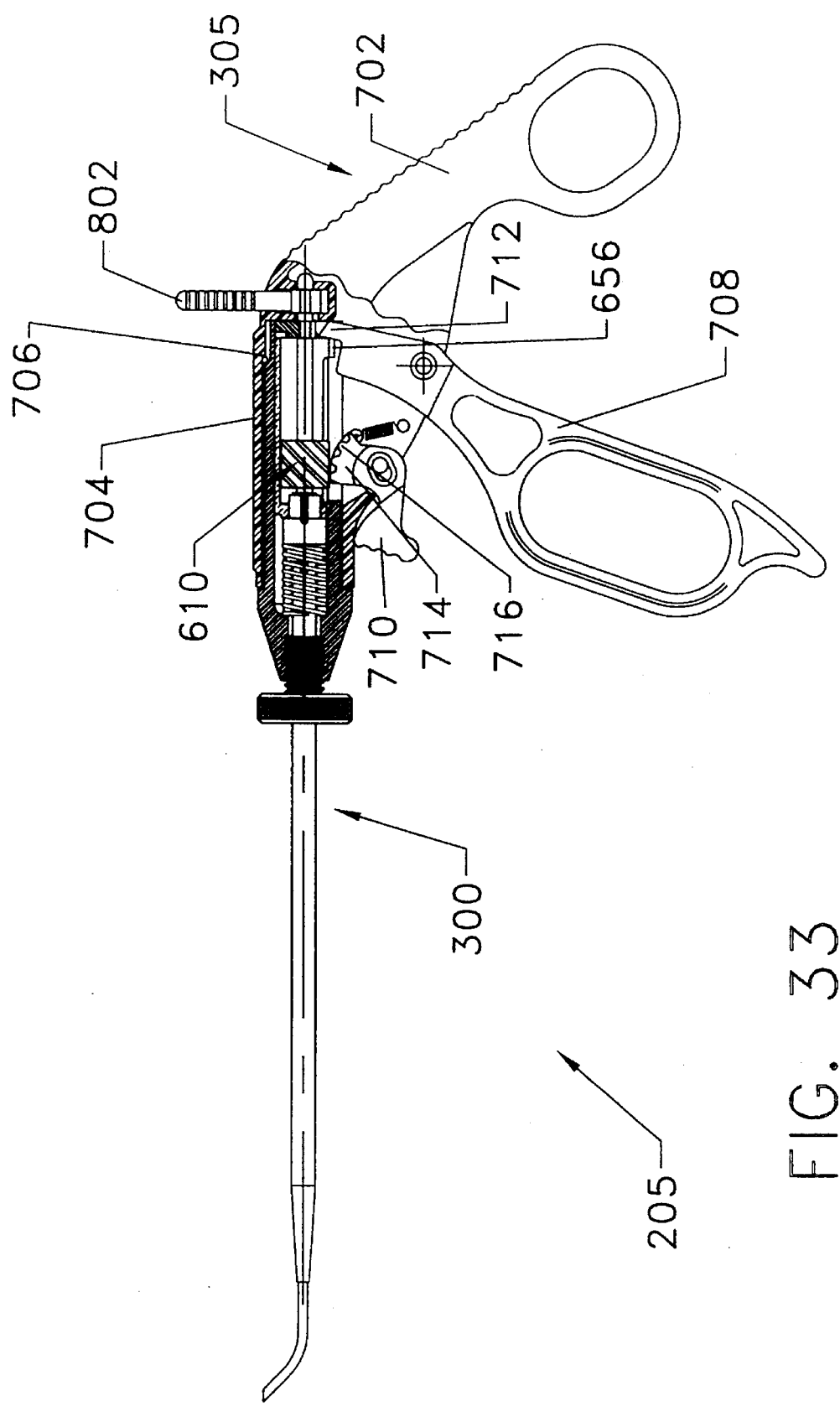
FIG. 33 a side view, partially cut away and partially in section, showing a second embodiment of the present invention, wherein the actuation means are positioned so as to place the two wire-like elements in their retracted position.
Figure 34:
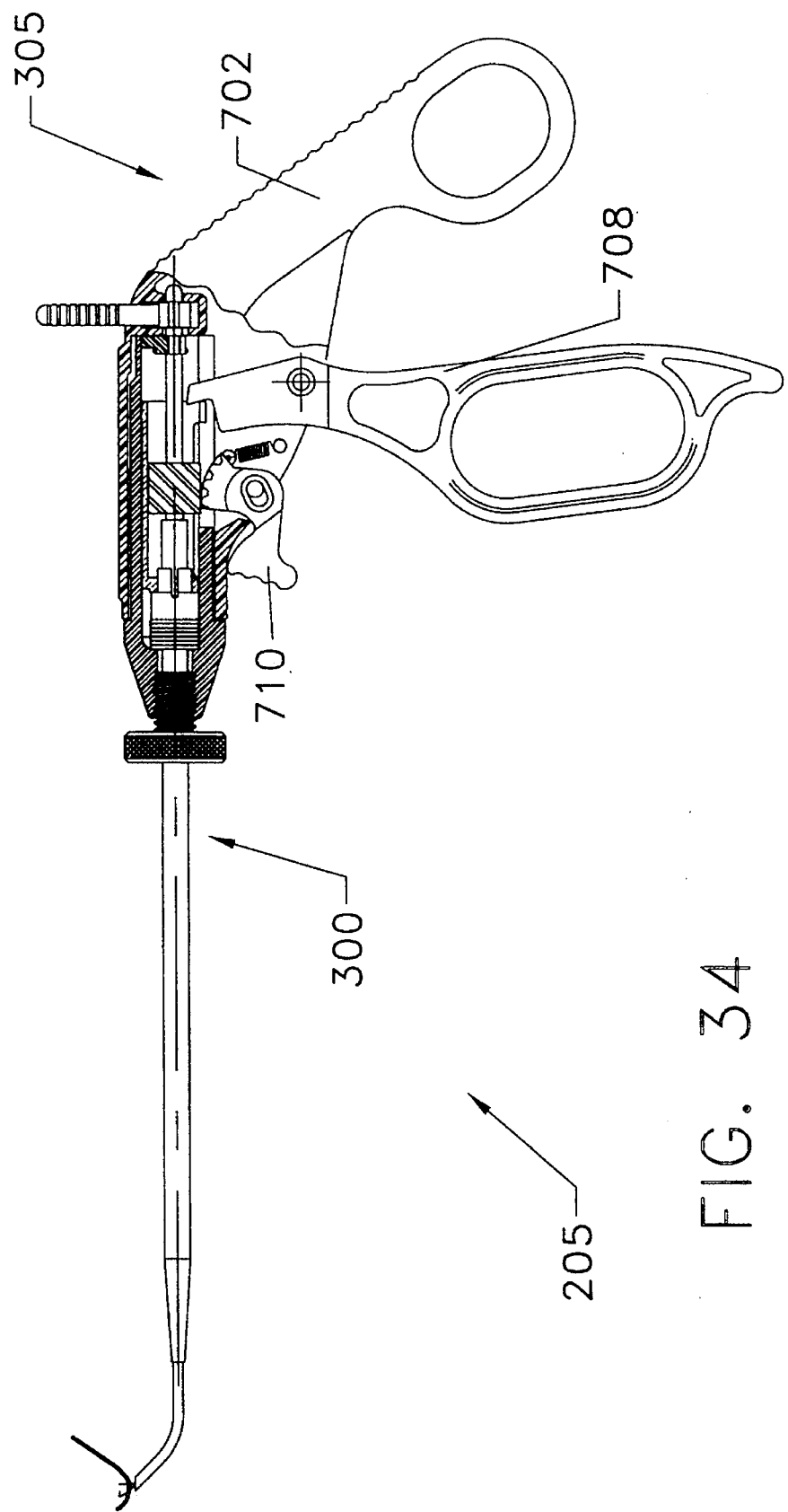
FIG. 34 is a view similar to that of FIG. 33, except that the actuation means are positioned so as to place the two wire-like elements in their fully extended, flared position.
Figure 35:
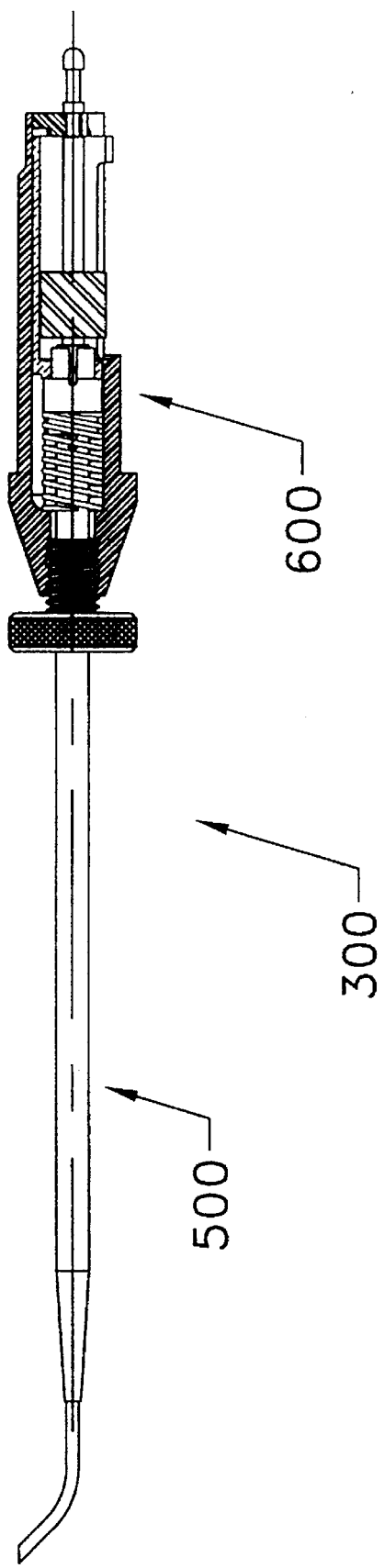
FIG. 35 is a side view in partial section showing a grasper assembly formed in accordance with the present invention, wherein the grasper device is the same as that shown in FIGS. 33 and 34.
Figure 36:
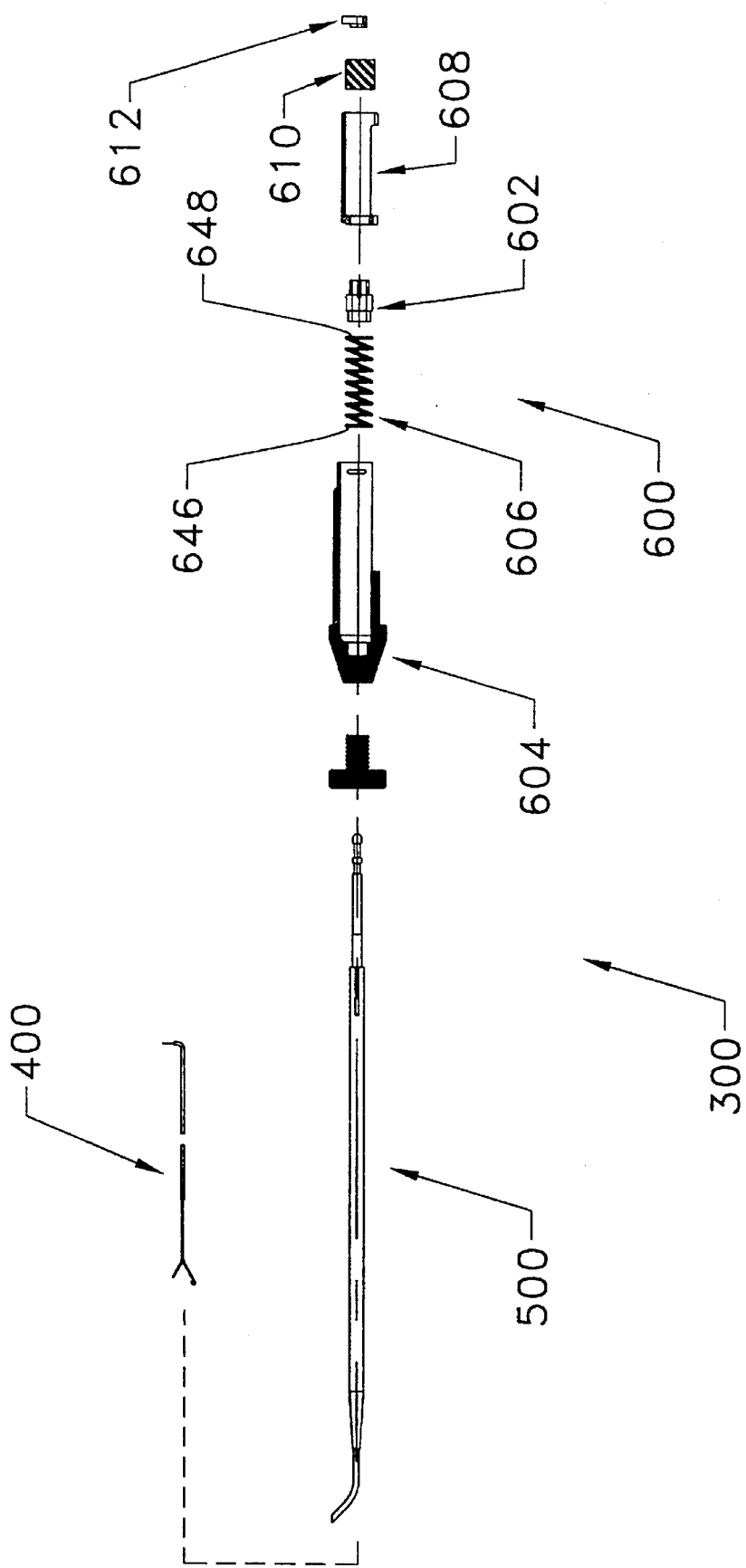
FIG. 36 is an exploded view of the grasper assembly shown in FIG. 35.

In some situations it may be desirable to be able to adjust the orientation of the distal portion of the shaft without changing the orientation of the tool's handle. Another preferred embodiment of the invention addresses this situation. In this embodiment, the device 205 (best seen in FIGS. 33 and 34) comprises a suture grasper assembly 300 (best seen in FIG. 35) and an actuation means 305 (best seen in FIGS. 33 and 34). More particularly, and as best seen in FIG. 36, suture grasper assembly 300 includes a wire subassembly 400, a shaft subassembly 500 and a housing subassembly 600.

Figure 37:
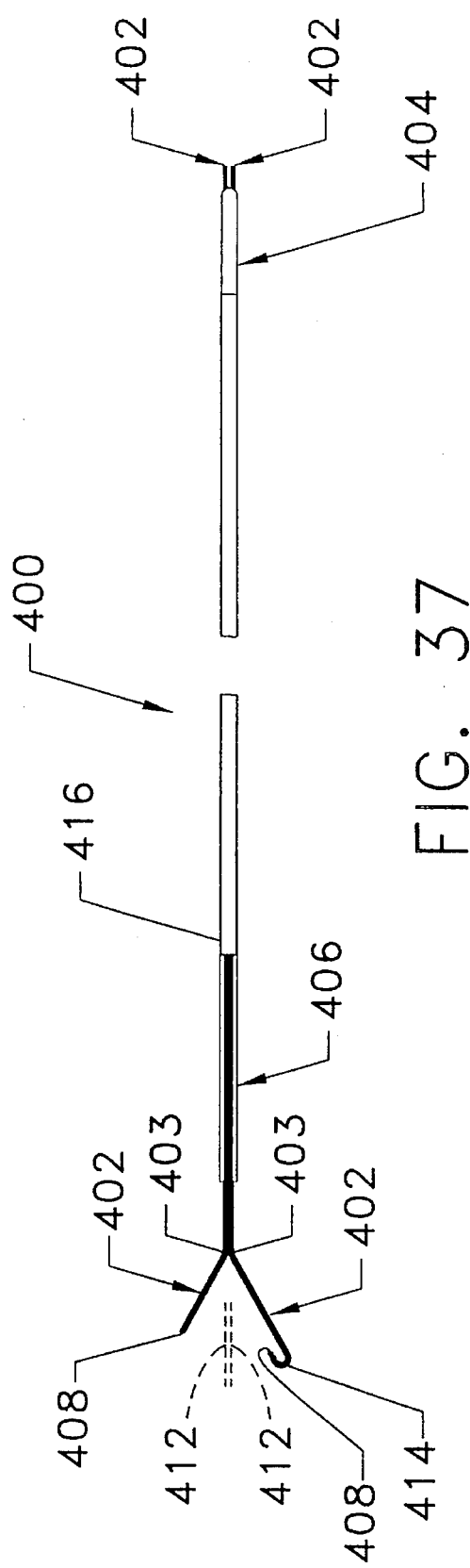
FIG. 37 is a side view of a wire subassembly suitable for use in the grasper assembly shown in FIG. 35.
Figure 38:
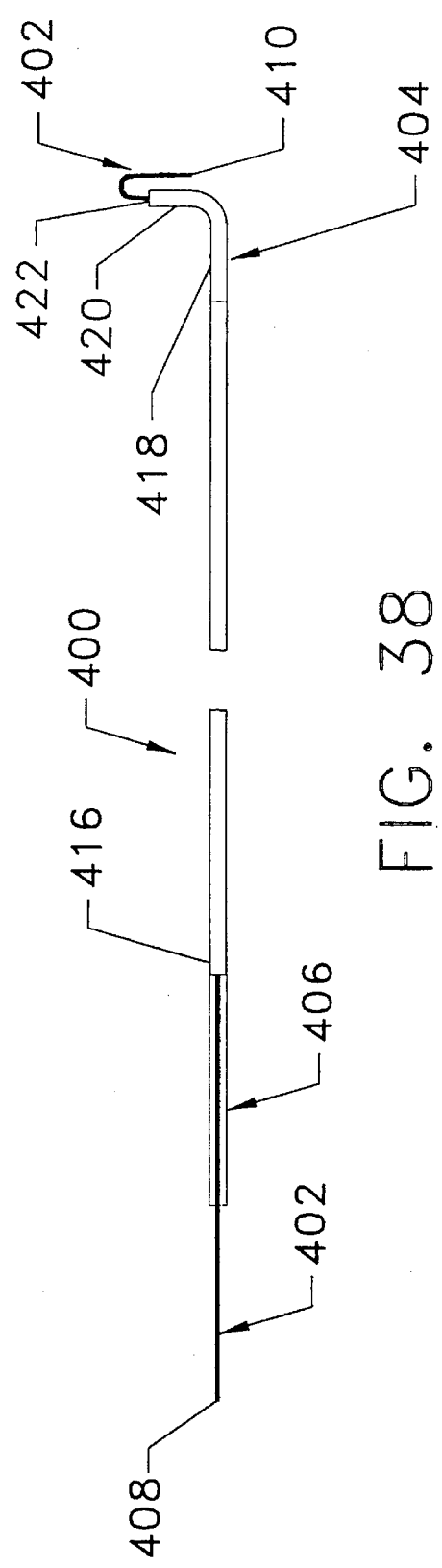
FIG. 38 is a top view of the wire subassembly shown in FIG. 37.

Wire subassembly 400 (best seen in FIGS. 37 and 38) includes at least one wire 402, a rigid tube 404 and a flexible sheath 406. Each of the wires 402 has a distal end 408, a proximal end 410 and a principle longitudinal axis 412. Further, each wire 402 defines a bend 403 at an angle of about 30° relative to its principle longitudinal axis 412. Bend 403 is located close to the wire's distal end 408. Each wire 402 has an equal length as measured between its proximal end 410 and its bend 403. In the case where only a single wire 402 is used, wire 402 is bent substantially adjacent to its distal end 408 so as to form a hook-like configuration 414. In the case where multiple wires 402 are used, at least one of the wires 402 is bent so as to form a hook-like configuration 414 as just described.

Tube 404 is typically made of stainless steel. It includes a distal end 416, a substantially straight distal portion 418 adjacent to distal end 416, and a substantially straight proximal portion 420 which extends at a substantially right angle to distal portion 418. Tube 404 terminates at a proximal end 422. Each of the wires 402 is secured to the proximal end 422 of tube 404. Each of the wires 402 also extends through both the distal and proximal portions 418, 420 of tube 404 so that bend 403 is spaced distally from distal end 416 of tube 404.

Flexible sheath 406 is made of a heat shrink material, and has an axial length greater than the separation of bends 403 of wires 402 and distal end 416 of tube 404. Flexible sheath 406 tightly covers the wires 402 and overlaps distal end 416 of tube 404. Accordingly, sheath 406 secures wires 402 together such that the portions of the wires located distally of bends 403 flare outwardly relative to one another, and the portions of the wires located immediately proximally of bends 403 can flex relative to their respective longitudinal axes 412.

Figure 39:
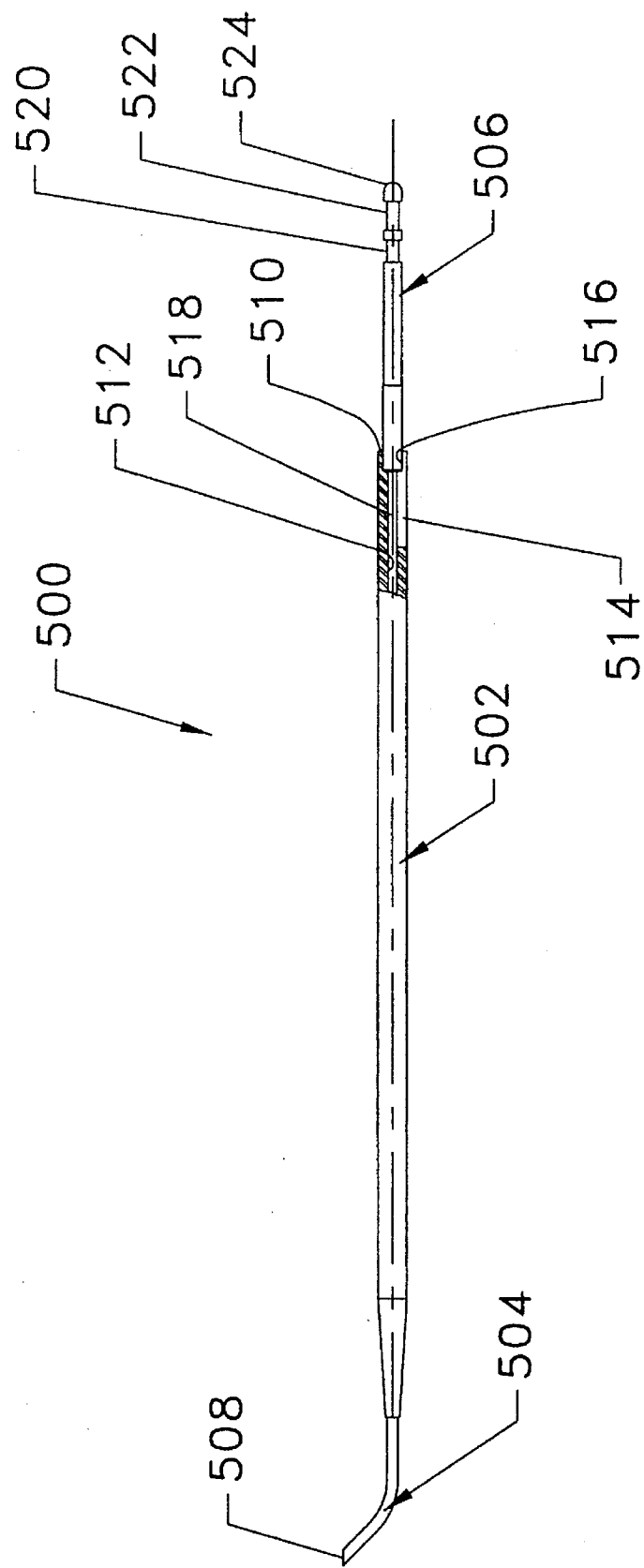
FIG. 39 is a side view, partially in section, of a shaft subassembly suitable for use in the grasper assembly shown in FIG. 35.

Shaft subassembly 500 (best seen in FIG. 39) includes a hollow shaft 502, a normally curved tip 504 and a drive rod 506. Shaft 502 has a distal end 508 and a proximal end 510, and defines an inner lumen 512 which has a substantially constant diameter along its length. Shaft 502 also includes a longitudinal slot 514 which extends distally from proximal end 510. Further, a counterbore 516 extends distally from proximal end 510 of shaft 502. One end 518 of drive rod 506 is received in counterbore 516, and is secured therein by any convenient and reliable means, e.g. by welding. A pair of circumferential grooves 520, 522 are provided in drive rod 506 adjacent to its proximal end 524.

Wire subassembly 400 is located in lumen 512 of shaft 502 such that the proximal portion 420 of wire subassembly 400 extends through longitudinal slot 514, and is reciprocally movable within slot 514. The length of wire subassembly 400 (as measured between proximal portion 420 and bends 403) is selected such that when proximal portion 420 of wire subassembly 400 engages the distal end of slot 514, the flared portions of wires 402 will extend beyond distal end 508 of shaft 502. Further, the longitudinal length of slot 514 is selected such that when proximal portion 420 of wire subassembly 400 engages distal end 518 of drive rod 506, the flared portions of wires 402 will reside within lumen 512 of shaft 502.

Housing subassembly 600 (see FIG. 36) includes a bearing 602, an outer housing 604, a compression spring 606, an inner housing 608, a cylindrical gear 610 and an end cap 612.

Bearing 602 (best seen in FIGS. 40–42) is a hollow cylindrical member having a proximal end 614, a distal end 616, and an outer surface 618. The hollow center of bearing 602 is adapted to receive shaft 502 therethrough. The outer surface 618 is relieved adjacent to proximal end 614 and adjacent to distal end 616 so as to define a pair of oppositely facing annular shoulders 620, 622 separated by a middle portion 624. Further, a longitudinal slot 626 extends from proximal end 614 to a closed end 628 located in middle portion 624. Slot 626 has a width slightly greater than the diameter of proximal portion 420 of wire subassembly 400. Accordingly, bearing 602 may be telescoped over distal end 508 of shaft 502 so that the proximal portion 420 of wire subassembly 400 (which projects through slot 514 in shaft 502) engages closed end 628 of bearing slot 626.

Outer housing 604 (best seen in FIGS. 43 to 46) includes a distal end wall 630 having a central opening 632 therethrough, an open proximal end 634, and a cylindrical side wall 636, which elements together define a substantially cylindrical, open-ended cavity 638. A longitudinal slot 640 extends distally from proximal end 634 for about one-half of the axial length of outer housing 604. The width of slot 640 is approximately the same as would be achieved by the removal of about 90° of side wall 636. In addition, a threaded counterbore 642 is formed around the distalmost portion of opening 632.

Compression spring 606 (best seen in FIG. 36) is located within distal portion 644 of cavity 638 such that one end 646 of the spring bears against distal end wall 630 of outer housing 604 about opening 632. Shaft subassembly 500 (carrying bearing 602 as described above) is inserted distal end first through housing open end 634, through spring 606, and through housing opening 632. As a result of this construction, the other end 648 of spring 606 bears against shoulder 622 of bearing 602.

Inner housing 608 (best seen in FIGS. 47 to 50) is reciprocally located within cavity 638 of outer housing 604.

Inner housing 608 includes a substantially circular distal end wall 650 having a centered opening 652 therethrough, a side wall 654 extending proximally from distal end wall 650, and a proximal end 665. A pair of opposing projections 656, 658 extend circumferentially into gap 660 from side edges 662, 664 of sidewall 654. If desired, the alignment of gap 660 of inner housing 608 with slot 640 of outer housing 604 may be assured by the provision of a groove 666 in distal end wall 650. Groove 666 will receive an elongated, longitudinal projection 667 formed on outer housing 404. Furthermore, the distal end wall 650 receives the relieved proximal portion of bearing 602 such that the distally facing surface of distal end wall 650 bears against shoulder 620 of bearing 602, thereby trapping proximal portion 420 of wire subassembly 400 in bearing slot 626.

A cylindrical gear 610 (best seen in FIGS. 51 and 52) resides on drive rod 506 within inner housing 608. Gear 610 includes an axial opening 668 which is adapted to receive drive rod 506. Gear 610 is made out of a substantially resilient material so that it elastically engages the outer surface of the drive rod. Outer surface 669 of gear 610 carries a plurality of generally helical flights 670. Accordingly, while gear 610 may slide along drive rod 506 somewhat during the projection and/or retraction of wire subassembly 500, its engagement with drive rod 506 is such that applied forces tending to rotate gear 610 also tend to rotate shaft 502.

Figure 54:
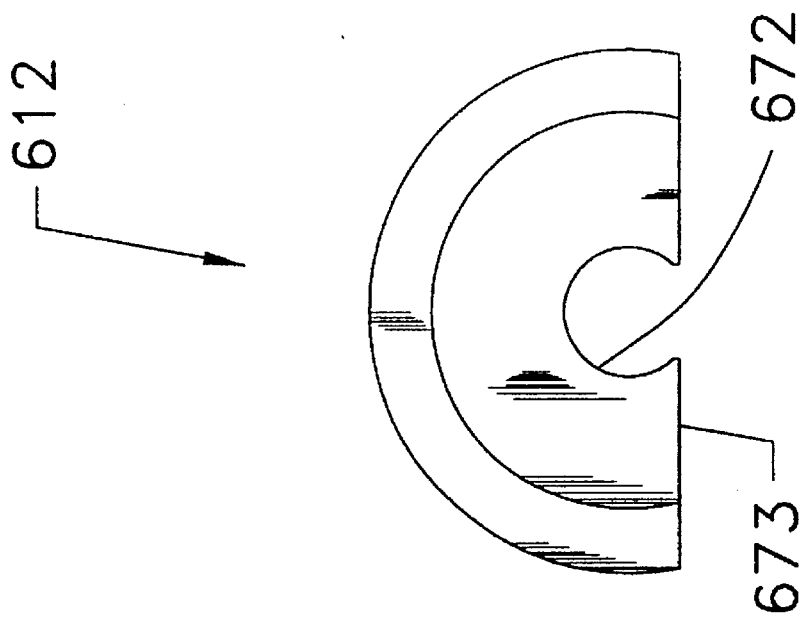
FIG. 54 is a left end view of the end cap shown in FIG. 53.
Figure 53:
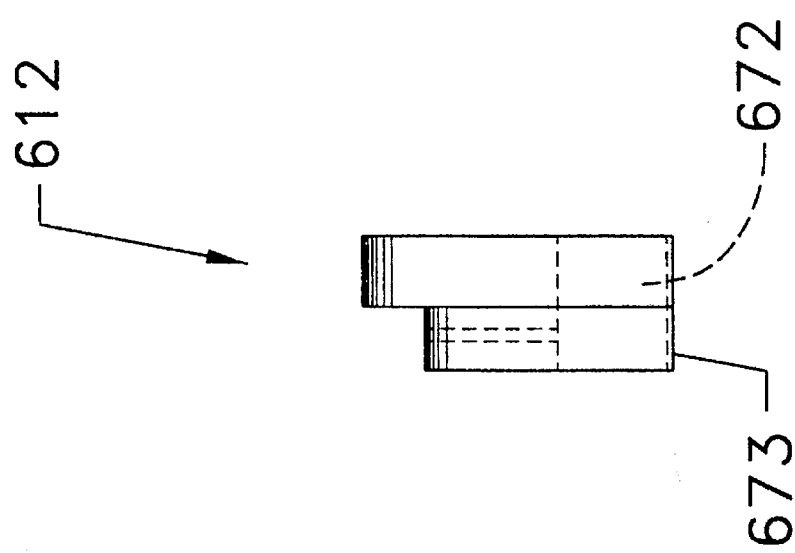
FIG. 53 is a side view of an end cap suitable for use in the grasper assembly shown in FIG. 35.

End cap 612 (best seen in FIGS. 53 and 54) is a generally semi-cylindrical member adapted to lock the elements of housing subassembly 600 together. To accomplish this, an opening 672 is provided midway along flat edge 673 of the cap's semi-cylindrical structure. The opening 672 is adapted to engage the drive rod's circumferential groove 520 adjacent to its distal end 524. Further, the periphery of cap 612 is adapted to engage sidewall 636 of outer housing 604 in a snap-fit or other secure manner.

Since there may be some play among the components of suturing device 205, and since such play can prove inconvenient when penetrating hard tissue with the sharp distal tip of the device, a lock nut 674 (best seen in FIGS. 55 to 57) also may be provided. Lock nut 674 can lock shaft subassembly 500 against rotation relative to actuation means 305. Lock nut 674 includes a cylindrical shaft 676 having a distal end 678, a proximal end 680, an outer surface 682 carrying threads 684, and an annular flange 686 extending radially outwardly from cylindrical shaft 676 adjacent to distal end 678. Cylindrical shaft 676 also includes a pair of opposing longitudinal slots 688, 690 extending distally from proximal end 680 to closed ends 692. Further, annular flange 686 defines an outer edge 694 which may be knurled to facilitate rotation of lock nut 674.

Lock nut 674 is telescoped proximal end first onto the distal portion of shaft subassembly 500 and moved into engagement with threaded counterbore 642 in outer housing 604. The outer diameter of shaft 676 and the diameter of counterbore 642 are selected such that as the lock nut's shaft 676 is progressively screwed into counterbore 642, the portions of the lock nut located between slots 688 and 690 will be squeezed inwardly against shaft 502. Accordingly, shaft 502 may rotate about its longitudinal axis when the lock nut engages only the distalmost portion of counterbore 642, but is prevented from rotating relative to outer housing 604 when the lock nut's shaft 676 is fully engaged within counterbore 642.

It will, therefore, be seen that the suture grasper assembly 300 normally retains the wire(s) 402 in their retracted position within shaft subassembly 500. Specifically, compression spring 606 normally urges inner housing 608 against end cap 612. Since the proximal portion 420 of wire subassembly 400 engages bearing 602 which is rotatably located in the central opening 652 in distal end wall 650 of inner housing 608, proximal portion 420 of wire subassembly 400 is urged against end 518 of drive rod 506 when inner housing 608 is in its proximalmost position within outer housing 604.

Actuation means 305 comprises a handle 702, a third housing 704 defining a substantially cylindrical cavity 706, and a pair of triggers 708 and 710 pivotally mounted to third housing 704. Third housing 704 is adapted to receive outer housing 604 such that (i) an end 712 of first trigger 708 engages the circumferential projections 656, 658 of inner housing 608, and (ii) a curved end 714 of second trigger 710 (carrying spaced teeth 716) engages gear 610. Further details of the construction of actuation means 305 are set forth in copending U.S. patent application Ser. No. 07/959,121, which is presently assigned to Innovasive Devices, Inc. of Hopkington, Mass., which is also the assignee of this application. U.S. patent application Ser. No. 07/959,121 is specifically incorporated herein by reference.

In view of the foregoing construction, a surgeon may grasp handle 702 and rotate first trigger 708 toward handle 702 with one hand. As first trigger 708 is rotated in this fashion, inner housing 608 is urged along shaft subassembly 500 toward distal end wall 630 of outer housing 604. This movement takes place against the force of spring 606. Movement of inner housing 608 relative to outer housing 604 causes proximal portion 420 of wire subassembly 400 to be urged distally along slot 514. This movement of proximal portion 420 of wire subassembly 400 urges the distal ends of wire-like elements 402 to project out the distal end 508 of shaft subassembly 500, for use in grasping a suture as described above.

When the surgeon wishes to rotate shaft subassembly 500 relative to actuation means 305, the surgeon pulls second trigger 710 toward handle 702. Such manipulation of second trigger 710 causes gear 610 to rotate within inner housing 608. Since gear 610 is mounted in substantially tight elastic contact around the distal portion of drive rod 506, the rotation of gear 610 causes axial rotation of shaft subassembly 500 and wire subassembly 400 as a unit.

Accordingly, the surgeon may, with one hand, (i) rotate a curved tip of the shaft subassembly about the longitudinal axis of the tool so that it faces in any desired radial direction, and/or (ii) move the wire subassembly from its retracted position toward its fully extended position. Further, since bearing 602 (holding proximal portion 420 of wire subassembly 400) is axially rotatable relative to opening 652 in distal end wall 650 of inner housing 608, bearing 602 will rotate with the shaft subassembly 500, thereby avoiding undesirable twisting of the subassembly 400.

Numerous changes, alterations, variations, and modifications may be made to the foregoing embodiments without departing from the scope of the present invention. Thus, for example, the shaft subassembly may include a lumen having an elliptical cross-section, rather than a circular transverse cross-section, in order to better accommodate wire-like elements 402 (see FIG. 58). Further, instead of locating the outwardly flaring portions of the wire-like elements 402 in the same plane, those portions may be located in adjacent parallel planes (see FIG. 59). Still further, instead of utilizing one wire-like element 402 with a hook at its distal end and another wire-like element 402 without a hook at its distal end, a single wire-like element 402 having a hook at its distal end might be used (see FIG. 60). Similarly, each wire-like element 402 may be hooked at its distal end (see FIG. 61), and the lengths of the wire-like elements may be selected such that the hooks overlap one another during closure (see FIG. 62), or such that the hook of one wire-like element resides within a projection of the area enclosed by the hook of the other wire-like element during closure (see FIG. 63). In addition, small ball-like enlargements 800 may also be placed at the ends of the wire-like elements 402. These enlargements 800 will help prevent the wire-like elements from spearing any braided suture or tissue which may be engaged by the tips of the wires.

In addition, the actuation means may also be provided with an electrical connection 802 (see FIG. 33) at the closed end of its housing 704. In that case, proximal end 524 of shaft subassembly 500 would engage electrical connection 802, and shaft 502 and outer housing 604 of the grasper assembly and housing 704 of the actuation means 305 would be formed of insulating material. This alternative would allow the device to be used in cauterization procedures as well as in grasping and suturing procedures.

It should be understood that the foregoing specification has been presented by way of illustration and not limitation. It is intended that the present invention should be limited only by the terms of the claims appended hereto.

What is claimed is:

1. A device for grasping a filament-like object comprising:

a wire assembly comprising at least one wire-like element having a distal end, a proximal end, and object capturing means for capturing said object adjacent to said distal end of said at least one wire-like element, and a rigid tube having a longitudinal axis, a distal end and a proximal end;

said tube being bent at a substantially right angle to said longitudinal axis at a point spaced from said proximal end of said tube so as to form a generally L-shaped configuration having a long leg and a short leg, said proximal end of said wire-like element being attached to said proximal end of said tube and extending through said tube such that said wire-bike element at least in part extends out of said distal end of said tube;

a hollow shaft adapted to substantially contain said wire assembly, said shaft having a pointed distal end, a proximal end, and a longitudinal slot having a distal end and a proximal end;

said slot being adapted to receive said short leg of said L-shaped tube, said proximal end of said slot being located at an axially measured distance from said distal end of said shaft, and said distal end of said slot being located at an axially measured distance from said distal end of said shaft, such that when said tube short leg engages said distal end of said slot, portions of said wire-like element extend beyond said distal end of said shaft, and when said wire assembly short leg is disposed proximate said proximal end of said slot, said wire-like element is disposed within said shaft; and actuation means attached to said proximal end of said shaft and to said short leg of said L-shaped tube for (i) reciprocally moving said L-shaped tube between a first position wherein said capturing means is contained within said shaft and a second position wherein said capturing means extend out of said distal end of said shaft, and (ii) rotating said wire assembly and said shaft as a unit abut said longitudinal axis of said shaft.

2. A device according to claim 1 wherein said distal end of said shaft is curved.

3. A device according to claim 1 wherein said actuation means includes spring biasing means for urging said at least one wire-like element toward said first position.

4. A device according to claim 1 wherein said distal end of said shaft is located in a plane disposed at an angle to said longitudinal axis.

5. A device according to claim 1 wherein said wire assembly comprises at least two wire-like elements, the distal portions of said at least two wire-like elements normally flare outwardly from one another in the same plane, and further wherein a first of said wire-like elements defines a hook adjacent to its distal end, and the second of said wire-like elements has a length such that when said tube and said shaft are in said first position, the distal end of said second wire-like element is closely spaced from said distal end of said first wire-like element.

6. A device according to claim 5 wherein said wire assembly further includes a ball-like enlargement disposed at said distal end of said first wire-like element.

7. A device according to claim 1 wherein said wire assembly includes at least two wire-like elements, the distal portions of said at least two wire-like elements normally flare outwardly from one another in adjacent parallel planes, and each of said wire-like elements defines a hook adjacent its distal end.

8. A device according to claim 1 wherein said wire assembly includes at least two wire-like elements, the distal portions of said at least two wire-like elements normally flare outwardly from one another, one of said wire-like elements is shorter than the other of said wire-like elements, and the distal portion of each said wire-like element defines a hook at its distal end, said hooks being adapted for location one inside the other when said tube and said shaft are in said first position.

9. A device according to claim 8 wherein each of said at least two wire-like elements further includes a ball-like enlargement disposed at its distal end.

10. A device according to claim 1 wherein said shaft is curved adjacent to its distal end, and said tube elastically grasps said at least one wire-like element and is flexible adjacent to its distal end.

11. A device according to claim 1 wherein said pointed distal end of said shaft comprises an end surface which is located in a plane disposed so as to form an acute angle with said longitudinal axis of .said shaft.

12. A device according to claim 11 wherein the angle of said surface to said longitudinal axis of said shaft is chosen such that a filament-like object held against said surface by said object capturing means when said device is biased toward said first position will not extend beyond said pointed distal end of said shaft.

13. A device according to claim 1 wherein said actuation means comprises a first housing assembly and a second housing assembly;

said first housing assembly comprising a first end wall and a first side wall defining a first open-ended, substantially cylindrical cavity, a handle extending radially outwardly from said first side wall adjacent to said first end wall, and first and second trigger members pivotally mounted to said first side wall distally of said handle, said first trigger defining at least one projection extending into said cavity, and said second trigger defining a series of projections adapted to sequentially extend into said cavity; and said second housing assembly comprising a second end wall having a central opening therethrough and a second side wall, said second side wall forming a second open-ended, substantially cylindrical cavity adjacent to said second end wall, a helical compression spring located in said second open-ended cavity, an inner housing comprising a third end wall defining a central opening therethrough and a third side wall extending proximally from about three-fourths of the periphery of said third end wall, a bushing having a proximal end and a distal end, said proximal end of said bushing being mounted for axial rotation in said opening in said third end wall and said distal end of said bearing engaging said helical spring, a substantially cylindrical member including helical gear flights on its outer surface located within said inner housing, and a substantially semi-circular end cap;

said second housing assembly being mounted on said proximal portion of said shaft such that said proximal portion of said shaft extends through said opening in said second end wall, through said helical spring, through said bushing, through said opening in said third end wall of said inner housing, through said cylindrical member in elastically gripping relation therewith, and through said end cap;

said second housing engaging said first cavity in telescopic relation therewith such that said projections from said first trigger engage said second rear wall and said projections from said second trigger engage said gear flights on said outer surface of said cylindrical member;

whereby rotation of said first trigger causes said inner housing to slide toward said second end wall against said compression spring, and rotation of said second trigger causes rotation of said cylindrical member, said shaft, said bushing and said wire.

14. A method for passing a filament-like object through tissue, said method comprising:

(a) providing a device for grasping a filament-like object, said device comprising:

first and second resilient wire-like elements, each having a distal end, a proximal end, and at least one of said elements having object capturing means for capturing the object to said distal end of said one element, said elements being biased to flare outwardly from each other;

a hollow shaft having a longitudinal axis, a pointed distal end, and a proximal end, said shaft being adapted to contain said wire-like elements wholly within said shaft, said hollow shaft being provided with a lumen extending from said distal end to said proximal end; and actuation means in mechanical communication with said proximal ends of said wire-like elements and attached to said proximal end of said shaft for reciprocally moving said wire-like elements between a first position wherein said wire-like elements are contained wholly within said shaft and a second position wherein said wire-like elements extend out of said distal end of said shaft and are flared away from each other such that said object capturing means of said one element is Spaced from the second of said elements to define therebetween a capture zone; and said device further comprises a solid rod having a distal end and a proximal end, said rod being positioned in said lumen in reciprocally sliding relationship therewith;

said first and second wire-like elements being attached at their respective proximal ends to said distal end of said rod so as to extend distally therefrom, said object capturing means comprising a hook-shaped configuration adjacent to said distal end of said one element, said distal ends of said first and second wire-like elements being spring biased to flare away from one another; and said actuation means is attached to said proximal end of said rod for moving said rod and said wire-like elements between said first position wherein said distal ends of said wire-like elements are contained wholly within said shaft, and said second position wherein said distal ends of said wire-like elements extend outwardly from said distal end of said shaft in flared relationship to one another;

(b) positioning said wire-like elements in said first position;

(c) inserting said shaft through said tissue;

(d) maneuvering said distal end of said shaft so that it is located substantially adjacent to said object;

(e) positioning said wire-like elements in said second position, and maneuvering said object capturing means so as to substantially surround said object;

(f) moving said wire-like elements toward said first position so as to grapple a portion of said object and thereby secure said object to said distal end of said shaft;

(g) withdrawing said shaft from said tissue so as to thread said object through said tissue; and (h) positioning said wire-like elements in said second position, and maneuvering said shaft so as to cause said object capturing means to release said object.

15. A method according to claim 14 wherein said device further comprises elongated portions of said elements extending from said proximal ends thereof joined together along their lengths and forming at least one of (i) at least in part said actuation means, and (ii) at least in part said rod.

16. A method for passing a filament-like object through tissue, the method comprising:

(a) providing a device for grasping a filament-like object, said device comprising:

a wire assembly comprising at least one wire-like element having a distal end, a proximal end, and object capturing means for capturing said object adjacent to said distal end of said at least one wire-like element, and a rigid tube having a longitudinal axis, a distal end, and a proximal end;

said tube being bent at a substantially right angle to said longitudinal axis at a point spaced from said proximal end of said tube so as to form a generally L-shaped configuration having a long leg and a short leg, said proximal end of said wire-like element being attached to said proximal end of said tube and extending through said tube such that said wire-like element at least in part extends distally outwardly from said distal end of said tube;

a hollow shaft having a longitudinal axis and adapted to substantially contain said wire assembly, said shaft having a pointed distal end, a proximal end, and a longitudinal slot having a distal end and a proximal end;

said slot being adapted to receive said short leg of said L-shaped tube, said proximal end of said slot being located at an axially measured distance from said distal end of said shaft, and said distal end of said slot being located an axially measured distance from said distal end of said shaft, such that when said tube short leg engages said distal end of said slot, portions of said wire-like element extend beyond said distal end of said shaft, and when said wire assembly short leg is disposed proximate said proximal end of said slot, said wire-like element is disposed within said shaft; and actuation means attached to said proximal end of said shaft and to said short leg of said L-shaped tube for (i) reciprocally moving said tube between a first position wherein said object capturing means is contained within said shaft and a second position wherein said object capturing means extend out of said distal end of said shaft, and (ii) rotating said wire assembly and said shaft as a unit about said longitudinal axis of said shaft;

(b) positioning said at least one wire-like element in said first position;

(c) inserting said shaft through said tissue;

(d) maneuvering said distal end of said shaft so that it is located substantially adjacent to said object;

(e) positioning said at least one wire-like element in said second position, and maneuvering said object capturing means so as to substantially surround said object;

(f) moving said at least one wire-like element toward said first position so as to grapple a portion of said object and thereby secure said object to said distal end of said shaft;

(g) withdrawing said shaft from said tissue so as to thread said object through said tissue; and (h) positioning said at least one wire-like element in said second position, and maneuvering said shaft so as to cause said object capturing means to release said object.

17. A method according to claim 16 wherein said distal end of said shaft is curved, and further including the step of rotating said shaft and said at least one wire-like element as a unit so as to present said pointed distal end of said shaft to said tissue at an optimally desired angle.

18. A method for passing a filament-like object through tissue, said method comprising:

(a) providing a device for grasping a filament-like object, said device comprising:

first and second resilient wire-like elements, each having a distal end, a proximal end, and at least one of said elements having object capturing means for capturing the object to said distal end of said one element, said elements being biased to flare outwardly from each other, said first and second resilient wire-like elements each further including a spherical enlargement disposed at its distal end;

a hollow shaft having a longitudinal axis, a pointed distal end, and a proximal end, said shaft being adapted to contain said wire-like elements wholly within said shaft; and actuation means in mechanical communication with said proximal ends of said wire-like elements and attached to said proximal end of said shaft for reciprocally moving said wire-like elements between a first position wherein said wire-like elements are contained wholly within said shaft and a second position wherein said wire-like elements extend out of said distal end of said shaft and are flared away from each other such that said object capturing means of said one element is spaced from a second of said elements to define therebetween a capture zone;

(b) positioning said wire-like elements in said first position;

(c) inserting said shaft through said tissue;

(d) maneuvering said distal end of said shaft so that it is located substantially adjacent to said object;

(e) positioning said wire-like elements in said second position, and maneuvering said object capturing means so as to substantially surround said object;

(f) moving said wire-like elements toward said first position so as to grapple a portion of said object and thereby secure said object to said distal end of said shaft;

(g) withdrawing said shaft from said tissue so as to thread said object through said tissue; and (h) positioning said wire-like elements in said second position, and maneuvering said shaft so as to cause said object capturing means to release said object.

* * * * *